(12) United States Patent
Skinkle et al.

(10) Patent No.: US 7,407,472 B2
(45) Date of Patent: Aug. 5, 2008

(54) CENTRIFUGE APPARATUS FOR PROCESSING BLOOD

(75) Inventors: David W. Skinkle, Denver, CO (US); Stephen W. Berch, Arvada, CO (US)

(73) Assignee: Sorin Group USA, Inc., Arvada, CO (US)

( * ) Notice: Subject to any disclaimer, the term of this patent is extended or adjusted under 35 U.S.C. 154(b) by 355 days.

(21) Appl. No.: 11/079,940

(22) Filed: Mar. 14, 2005

(65) Prior Publication Data

US 2006/0021952 A1 Feb. 2, 2006

Related U.S. Application Data

(63) Continuation-in-part of application No. 10/659,855, filed on Sep. 11, 2003, now Pat. No. 7,060,018.

(51) Int. Cl.
*B04B 7/08* (2006.01)
*B04B 11/00* (2006.01)

(52) U.S. Cl. .............. 494/2; 494/5; 494/37; 494/45

(58) Field of Classification Search ............... 494/18, 494/23–30, 38, 41, 43, 45, 47, 48, 50, 56, 494/37, 2, 5; 210/781, 782, 787, 512.1
See application file for complete search history.

(56) References Cited

U.S. PATENT DOCUMENTS

| | | | |
|---|---|---|---|
| 3,096,283 A | 7/1963 | Hein | 494/38 |
| 3,133,881 A | 5/1964 | Childs | |
| 3,145,713 A | 8/1964 | Latham, Jr. | |
| 3,239,136 A | 3/1966 | Hein | |
| 3,244,362 A | 4/1966 | Hein | 494/1 |
| 3,244,363 A | 4/1966 | Hein | 494/1 |
| 3,456,875 A | 7/1969 | Hein | 494/3 |
| 3,737,096 A | 6/1973 | Jones et al. | |

(Continued)

FOREIGN PATENT DOCUMENTS

DE 26 58 926 A1 6/1978

(Continued)

OTHER PUBLICATIONS

Dec. 14, 2004 Invitation to Pay Additional Fees and Partial International Search Report in PCT/US2004/029574 (7 pages).

(Continued)

*Primary Examiner*—Charles E Cooley
(74) *Attorney, Agent, or Firm*—Popovich, Wiles & O'Connell, P.A.

(57) ABSTRACT

A centrifuge apparatus for processing blood comprising a bottom spring-loaded support plate; a top support plate; an axial inlet/outlet for blood to be processed and processed components of the blood, the axial inlet/outlet being attached to the top support plate by a rotating seal assembly; a variable volume separation chamber mounted between the bottom support plate and the top support plate, the variable volume separation chamber being fluidly connected to the axial inlet/outlet; a pump fluidly connected to the axial inlet/outlet; and a rotary drive unit attached to the bottom support plate. The top support plate is fixed vertically and the bottom spring-loaded support plate is mounted on springs that maintain pressure on the variable volume separation chamber and allow the bottom support plate to move vertically.

27 Claims, 24 Drawing Sheets

U.S. PATENT DOCUMENTS

| | | | |
|---|---|---|---|
| 4,069,968 A | 1/1978 | Herman | 494/1 |
| 4,136,818 A | 1/1979 | Larrabee | 494/1 |
| 4,142,670 A | 3/1979 | Ishimaru et al. | 494/38 |
| 4,199,544 A | 4/1980 | Muhlbock et al. | 494/16 |
| 4,402,680 A | 9/1983 | Schoendorfer | |
| 4,416,654 A | 11/1983 | Schoendorfer et al. | |
| 4,417,884 A | 11/1983 | Schoendorfer et al. | |
| 4,421,503 A | 12/1983 | Latham, Jr. et al. | |
| 4,447,220 A | 5/1984 | Eberle | |
| 4,530,691 A | 7/1985 | Brown | |
| 4,646,167 A | 2/1987 | Denecke | |
| 4,683,579 A | 7/1987 | Wardlaw | |
| 4,724,317 A | 2/1988 | Brown | |
| 4,734,089 A | 3/1988 | Cullis | 494/27 |
| 4,810,090 A | 3/1989 | Boucher et al. | |
| 4,944,833 A | 7/1990 | Belt et al. | |
| 4,946,434 A | 8/1990 | Plaisted et al. | |
| 4,983,158 A | 1/1991 | Headley | |
| 5,053,127 A | 10/1991 | Schoendorfer et al. | |
| 5,171,456 A | 12/1992 | Hwang et al. | |
| 5,234,608 A | 8/1993 | Duff | |
| 5,356,365 A | 10/1994 | Brierton | 494/14 |
| 5,368,542 A | 11/1994 | McMannis et al. | 494/45 |
| 5,494,592 A | 2/1996 | Latham, Jr. et al. | |
| 5,529,691 A | 6/1996 | Brown | |
| 5,545,516 A | 8/1996 | Wagner | |
| 5,565,977 A | 10/1996 | Rosinko | |
| 5,605,842 A | 2/1997 | Langley | |
| 5,607,579 A | 3/1997 | Latham, Jr. et al. | |
| 5,637,082 A | 6/1997 | Pages et al. | |
| 5,651,766 A | 7/1997 | Kingsley et al. | |
| 5,658,240 A | 8/1997 | Urdahl et al. | |
| 5,690,815 A | 11/1997 | Krasnoff et al. | |
| 5,722,946 A | 3/1998 | Mudloff et al. | |
| 5,728,306 A | 3/1998 | Breillatt, Jr. et al. | |
| 5,733,253 A | 3/1998 | Headley et al. | |
| 5,779,660 A | 7/1998 | Kingsley et al. | |
| 5,783,085 A | 7/1998 | Fischel | |
| 5,792,372 A | 8/1998 | Brown et al. | |
| 5,824,216 A | 10/1998 | Joie et al. | |
| 5,830,133 A | 11/1998 | Osten et al. | |
| 5,837,150 A | 11/1998 | Langley et al. | |
| 5,849,178 A | 12/1998 | Holm et al. | |
| 5,853,382 A | 12/1998 | Kingsley et al. | |
| 5,872,627 A | 2/1999 | Miers | |
| 5,876,611 A | 3/1999 | Shettigar | |
| 5,895,575 A | 4/1999 | Kraus et al. | |
| 5,936,714 A | 8/1999 | Gibbs | |
| 5,954,971 A | 9/1999 | Pages et al. | |
| 5,958,250 A | 9/1999 | Brown et al. | |
| 5,980,757 A | 11/1999 | Brown et al. | |
| 5,993,370 A | 11/1999 | Brown et al. | |
| 6,007,472 A | 12/1999 | Schill et al. | |
| 6,007,509 A | 12/1999 | Kingsley et al. | |
| 6,039,711 A | 3/2000 | Headley et al. | |
| 6,071,423 A | 6/2000 | Brown et al. | |
| 6,074,335 A | 6/2000 | Headley et al. | 494/26 |
| 6,099,740 A | 8/2000 | Holm et al. | |
| 6,102,883 A | 8/2000 | Kingsley et al. | |
| 6,106,727 A | 8/2000 | Krasnoff et al. | |
| 6,123,655 A | 9/2000 | Fell | |
| 6,144,444 A | 11/2000 | Haworth et al. | |
| 6,174,447 B1 | 1/2001 | Spindler | |
| 6,175,420 B1 | 1/2001 | Barry et al. | |
| 6,183,651 B1 | 2/2001 | Brown et al. | |
| 6,200,287 B1 | 3/2001 | Keller et al. | |
| 6,228,017 B1 | 5/2001 | Brown | |
| 6,231,537 B1 | 5/2001 | Holmes et al. | |
| 6,254,784 B1 | 7/2001 | Nayak et al. | |
| 6,284,142 B1 | 9/2001 | Muller | |
| 6,285,450 B1 | 9/2001 | Thomas et al. | |
| 6,296,602 B1 | 10/2001 | Headley | |
| 6,312,607 B1 | 11/2001 | Brown et al. | |
| 6,315,707 B1 | 11/2001 | Smith et al. | |
| 6,319,471 B1 | 11/2001 | Langley et al. | |
| 6,322,709 B1 | 11/2001 | Krasnoff et al. | |
| 6,325,775 B1 | 12/2001 | Thom et al. | |
| 6,348,156 B1 | 2/2002 | Vishnoi et al. | |
| 6,361,518 B1 | 3/2002 | Brierton et al. | |
| 6,379,322 B1 | 4/2002 | Kingsley et al. | |
| 6,409,696 B1 | 6/2002 | Toavs et al. | |
| 6,419,822 B2 | 7/2002 | Muller et al. | |
| 6,439,577 B2 | 8/2002 | Jorgensen et al. | |
| 6,558,307 B2 | 5/2003 | Headley | |
| 6,602,179 B1 | 8/2003 | Headley et al. | 494/41 |
| 6,632,191 B1 | 10/2003 | Headley et al. | |
| 6,824,506 B1 | 11/2004 | Lamphere et al. | |
| 6,852,074 B1 | 2/2005 | Jorgensen et al. | 494/13 |
| 7,060,018 B2 * | 6/2006 | Skinkle et al. | 494/45 |
| 2002/0014462 A1 | 2/2002 | Muller | |
| 2002/0128585 A1 | 9/2002 | Cork et al. | |
| 2003/0125182 A1 * | 7/2003 | Headley et al. | 494/41 |
| 2003/0191005 A1 | 10/2003 | Coelho et al. | |
| 2005/0009680 A1 * | 1/2005 | Sacco et al. | 494/37 |
| 2005/0051466 A1 | 3/2005 | Carter et al. | |
| 2005/0054508 A1 | 3/2005 | Panzani et al. | |
| 2005/0059540 A1 * | 3/2005 | Skinkle et al. | 494/48 |
| 2006/0021952 A1 * | 2/2006 | Skinkle et al. | 210/787 |
| 2006/0040818 A1 * | 2/2006 | Jorgensen et al. | 494/45 |
| 2007/0213191 A1 * | 9/2007 | Chammas | 494/41 |

FOREIGN PATENT DOCUMENTS

| | | |
|---|---|---|
| WO | WO 87/06857 | 11/1987 |
| WO | WO 00/38762 | 7/2000 |
| WO | WO 01/03798 A1 | 1/2001 |

OTHER PUBLICATIONS

Mar. 31, 2005 Notification of Transmittal of the International Search Report and the Written Opinion of the International Searching Authority, or the Declaration in PCT/US2004/029574 (19 pages).

Written Opinion of the International Searching Authority for International Application No. PCT/US2004/029574 (9 pages), Apr. 4, 2005.

U.S. Appl. No. 60/485,015, filed Jul. 2, 2003, Carter et al. (62 pages).

Jan. 16, 2008 International Search Report in European counterpart Application No. EP 04 78 3707 (3 pages).

* cited by examiner

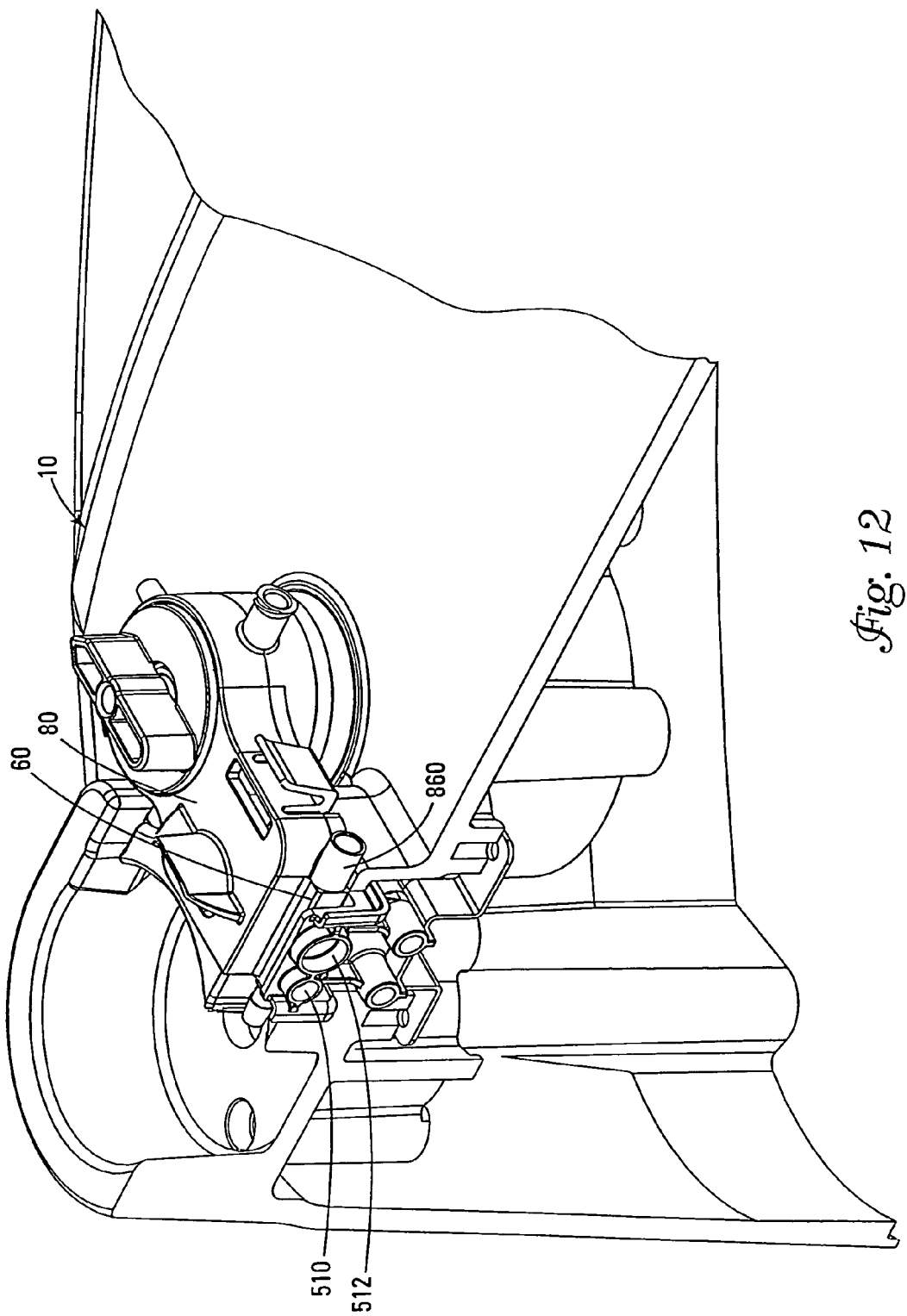

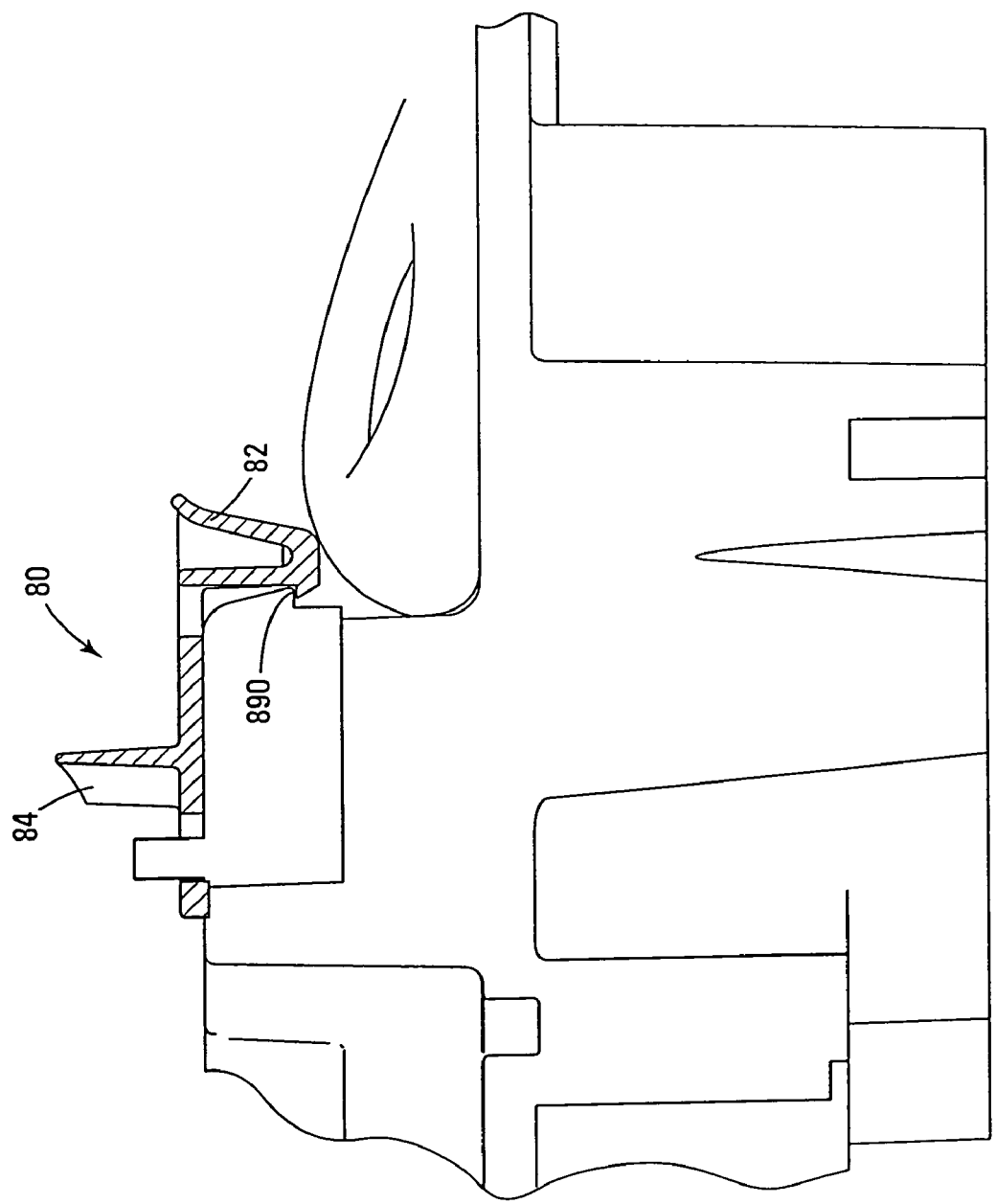

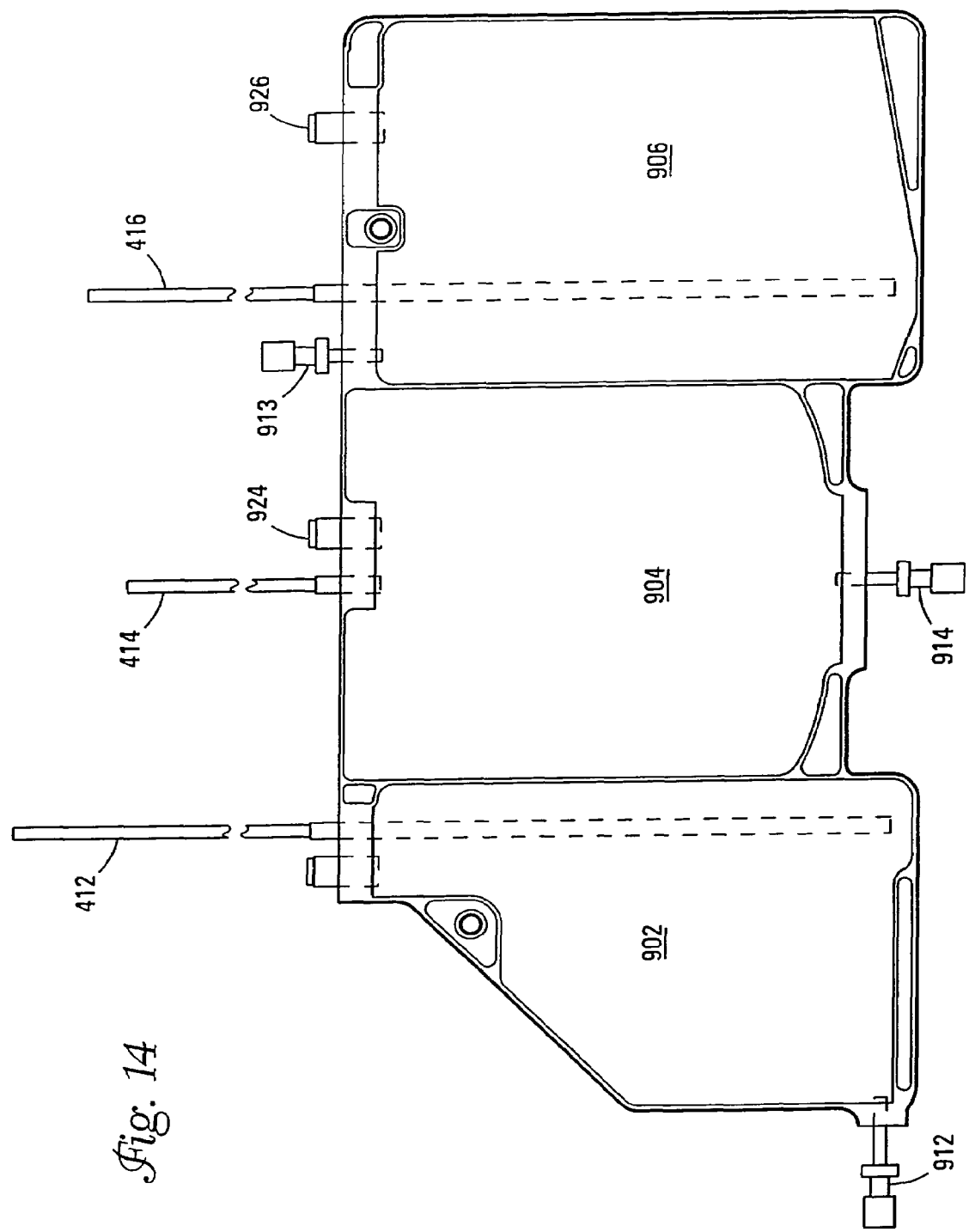

CENTRIFUGE APPARATUS FOR PROCESSING BLOOD

CROSS-REFERENCE TO RELATED APPLICATIONS

This application is a continuation-in-part of U.S. application Ser. No. 10/659,855, filed Sep. 11, 2003, now U.S. Pat. No. 7,060,018 B2, issued Jun. 13, 2006, the contents of which are hereby incorporated herein by reference.

FIELD OF THE INVENTION

This invention relates to an apparatus for separating components of whole blood. More particularly, this invention relates to an apparatus for the separation and collection of platelet poor plasma (PPP), platelet rich plasma (PRP), and red blood cells (RBC).

BACKGROUND OF THE INVENTION

Whole blood can be collected from a donor and processed into different products. The collection and separation of blood typically has involved many steps as well as operator interaction.

Whole blood contains red blood cells, white blood cells, platelets, and plasma. Traditionally, these components were separated by a batch process in which a blood bag was spun for a period of approximately 10 minutes in a large refrigerated centrifuge. After centrifugation, the main blood constituents, red blood cells (erythrocytes), platelets and white blood cells (leukocytes), and plasma sedimented and formed distinct layers. These constituents were then expressed sequentially by a manual extractor in different satellite bags attached to the primary bag.

More recently, automated extractors have been introduced. Nevertheless, the whole process remains laborious. There remains a widespread need for an apparatus that will automatically separate the different components of whole blood efficiently and easily.

SUMMARY OF THE INVENTION

The invention provides a centrifuge apparatus for processing blood comprising a bottom spring-loaded support plate; a top support plate; an axial inlet/outlet for blood to be processed and processed components of the blood, the axial inlet/outlet being attached to the top support plate by a rotating seal assembly; a variable volume separation chamber mounted between the bottom support plate and the top support plate, the variable volume separation chamber being fluidly connected to the axial inlet/outlet; a pump fluidly connected to the axial inlet/outlet; and a rotary drive unit attached to the bottom support plate. The top support plate is fixed vertically and the bottom spring-loaded support plate is mounted on springs that maintain pressure on the variable volume separation chamber and allow the bottom support plate to move vertically.

It is to be understood that both the foregoing general description and the following detailed description are exemplary and explanatory and are intended to provide further explanation of the invention as claimed.

BRIEF DESCRIPTION OF THE DRAWINGS

FIG. 12 is a cut-away partial detail view of the housing of the apparatus with the 4-way valve cartridge attached.

FIG. 13 is a partial cross-sectional view of the cartridge snapped on the housing.

FIG. 14 is a side view of the multicomponent 3-compartment reservoir bag.

DESCRIPTION OF THE PREFERRED EMBODIMENTS

Figure 1:
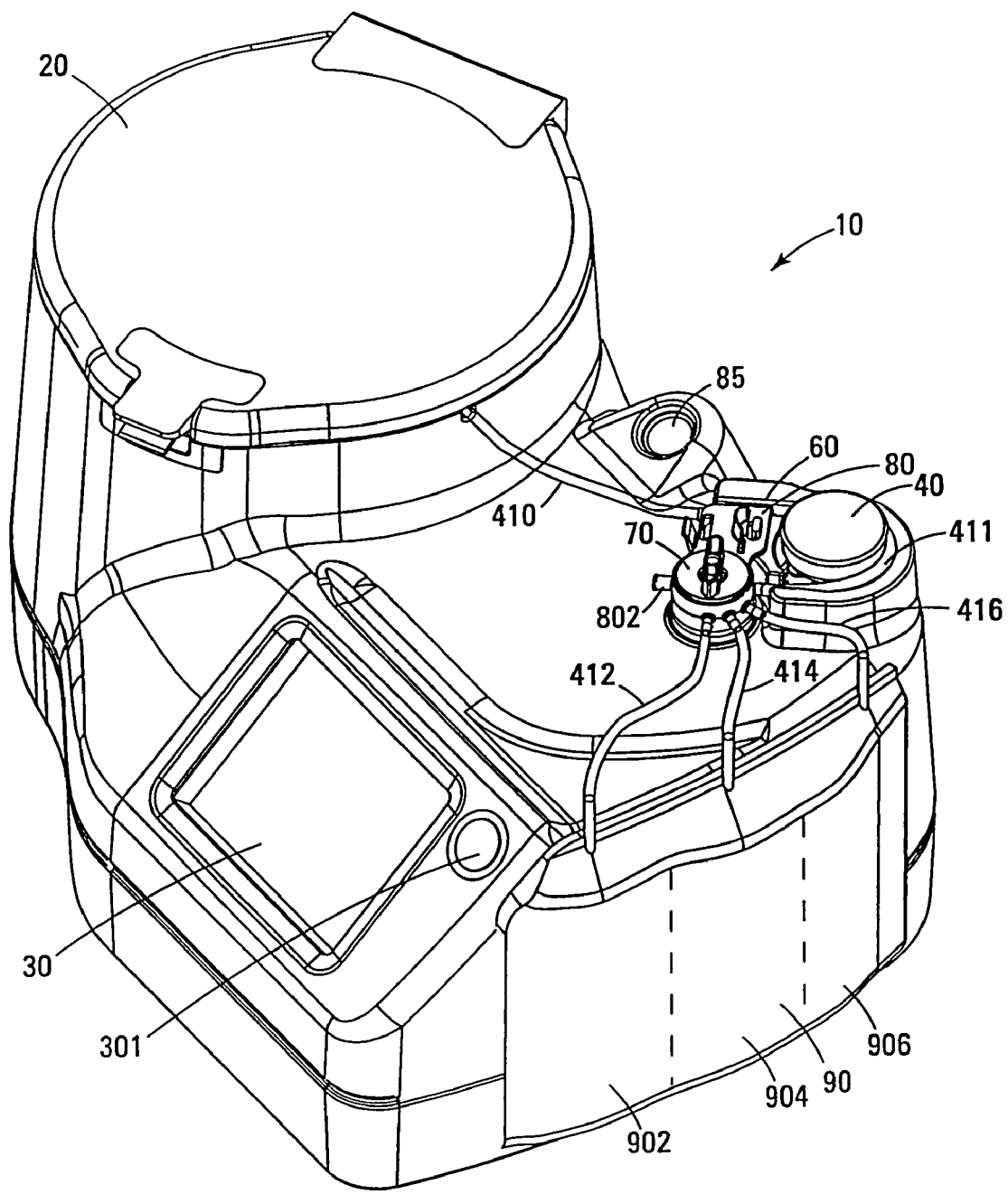
FIG. 1 is a perspective view of an apparatus of this invention.

In one embodiment, the invention provides an apparatus comprising a centrifuge with spring-loaded plate and top locking feature, a valve driver mechanism, fluid sensor, peristaltic pump and touch screen computer interface. Additionally, a syringe chiller may be provided to keep various components in a syringe at a desired temperature.

In a preferred embodiment, a single use, sterile disposable processing set interfaces with the apparatus. The sterile disposable consists of a circular variable volume separation chamber with axial rotating seal assembly, 4-way valve cartridge with integral sensor and fluid pump loop and a pre-attached three compartment reservoir bag. The three-compartment reservoir bag consists of a chamber for anticoagulated whole blood, a chamber for platelet poor plasma, and a chamber for concentrated red blood cells. Platelet rich plasma is collected in a sterile syringe attached to the 4-way valve luer lock port.

Specifically, the invention provides a centrifuge apparatus for processing anticoagulated whole blood comprising a bottom spring-loaded support plate, a slotted top locking feature, and a stator arm assembly. The disposable variable volume separation chamber with rigid support plate loads and locks into the spring loaded centrifuge chamber. The rotating seal of the separation chamber is interfaced and held stationary by the stator arm assembly. Tubing is attached to the rotating seal assembly to provide an axial inlet/outlet for blood to be processed and processed components of the blood. The 4-way valve assembly is attached to the inlet/outlet tube of the variable volume separation chamber. The 4-way valve is mounted to the fluid sensor and snaps to the top housing of the apparatus. Rotation of the peristaltic pump loads the fluid pump loop. The three compartment bag is attached to side of the apparatus to allow access to fluid inlet and outlet ports.

In a preferred embodiment, this invention achieves separation of whole blood components according to the following method of operation. The disposable processing set is attached to the apparatus. Whole blood collected from the donor is mixed with anticoagulant and delivered to the inlet port of the reservoir bag whole blood compartment. The clinician selects the desired whole blood volume to process on the user interface. The start button is selected to initiate the separation cycle and rotation of the centrifuge. The valve driver positions the 4-way valve to the whole blood compartment and the peristaltic pump drives fluid from the reservoir to the spinning variable volume separation chamber. Fluid pressure inside the rotating separation chamber increases with increased gravitational force and the addition of whole blood. This pressure drives the spring load bottom plate downward allowing additional volume to enter the rotating system. The flexible variable volume separation chamber changes shape and this shape change is limited by a fixed stop internal to the centrifuge housing. Once adequate separation of the whole blood components occurs, the centrifuge rotation speed is decreased. The peristaltic pump direction is reversed, pumping the component layers from the axial port of the separation chamber. The apparatus fluid sensor detects the concentration of the various component layers and utilizes algorithms to change the 4-way valve position to the desired component layer collection vessel. The process is complete when all component layers are collected and the apparatus fluid sensor senses air. The 4-way valve fluid path allows the draw back of platelet poor plasma from the PPP reservoir compartment into the PRP syringe. Multiple whole blood separation cycles are possible with this invention.

The advantages of this invention include the use of an automated system and the ability to separate variable quantities of blood. Even very small quantities of whole blood can be efficiently separated, collected, and returned to a patient using the apparatus of this invention. Larger volumes can also be selected and processed within approximately the same cycle time of smaller volumes, allowing the clinician to harvest a larger quantity of platelets per cycle. This is advantageous in patients with low platelet counts where more whole blood can be collected and processed in approximately the same cycle time with less dilution of the PRP product to produce substantially higher baseline multiples.

Additional advantages include the use of the fluid sensor to produce a PRP and PPP product void of red blood cells. The first component layer removed from this apparatus after centrifugation is the PPP layer. The fluid sensor detects when the PPP product is clear and free of red cells prior to collection. The same is true for the PRP collection. Once platelets are sensed the platelet collection process is initiated and continues until red blood cells are sensed. The user can predetermine the concentration of red blood cells in the final PRP product. This is advantageous in certain clinical procedures.

The invention provides a centrifuge apparatus for processing blood comprising a bottom spring-loaded support plate; a top support plate; an axial inlet/outlet for blood to be processed and processed components of the blood, the axial inlet/outlet being attached to the top support plate by a rotating seal assembly; a variable volume separation chamber mounted between the bottom support plate and the top support plate, the variable volume separation chamber being fluidly connected to the axial inlet/outlet; a pump fluidly connected to the axial inlet/outlet; and a rotary drive unit attached to the bottom support plate. The top support plate is fixed vertically and the bottom spring-loaded support plate is mounted on springs that maintain pressure on the variable volume separation chamber and allow the bottom support plate to move vertically.

The invention provides a method of processing blood comprising: providing a centrifuge apparatus as described above; introducing a quantity of blood into the variable volume separation chamber; centrifuging the blood; and removing the separated components of the blood through the axial inlet/outlet.

The invention also provides a centrifuge apparatus for processing blood comprising a bottom support plate; a top support plate; an axial inlet/outlet for blood to be processed and processed components of the blood, the axial inlet/outlet being attached to the top support plate by a rotating seal assembly; a variable volume separation chamber mounted between the bottom support plate and the top support plate, the variable volume separation chamber being fluidly connected to the axial inlet/outlet; a pump fluidly connected to the axial inlet/outlet; and a rotary drive unit attached to the bottom support plate. The top holder is fixed vertically and the bottom support plate is mounted on a ball-screw actuator that maintains pressure on the variable volume separation chamber and allows the bottom support plate to move vertically.

The invention provides a disposable cartridge comprising a plurality of ports for receiving or dispensing blood or blood components and a fluid sensor pathway for displaying blood or blood components for analysis, the cartridge being adapted to be mounted on a multi-position valve for directing flow between the ports and the fluid sensor pathway being adapted to be mounted adjacent to one or more sensors for analyzing blood.

The invention provides a disposable set comprising: a container for blood; a plurality of containers for receiving separated components of the blood; a disk-shaped bag; a top support plate for a centrifuge; an axial inlet/outlet for blood to be processed and processed components of the blood, the axial inlet/outlet being attached to the top support plate by a rotating seal assembly; and tubing. The disposable set may further comprise a disposable cartridge comprising a plurality of ports for receiving or dispensing blood or blood components and a fluid sensor pathway for displaying blood or blood components for analysis, the cartridge being adapted to be mounted on a multi-position valve for directing flow between the ports and the fluid sensor pathway being adapted to be mounted adjacent to one or more sensors for analyzing blood.

The invention provides a method of producing platelet rich plasma comprising: providing a centrifuge apparatus; introducing a quantity of blood into the centrifuge apparatus; centrifuging the blood; and removing a platelet rich plasma portion from the centrifuge apparatus. The final hematocrit of the platelet rich plasma portion is selected from a range of hematocrit values and the appropriate amount of additional red blood cells are added to the platelet rich plasma portion. In one embodiment of the invention, the final hematocrit selected is within the range of from 0 to 25. In another embodiment, the final hematocrit selected is within the range of from 5 to 25.

The invention provides a method of producing platelet rich plasma comprising: providing a centrifuge apparatus; introducing a quantity of blood into the centrifuge apparatus; centrifuging the blood; and removing a platelet rich plasma portion from the centrifuge apparatus. A spin time and a rotational speed of the centrifuge apparatus are automatically selected based on the volume of blood introduced into the centrifuge apparatus. In one embodiment of the invention, a first and second spin time and a first and second rotational speed are automatically selected based on the volume of blood introduced into the centrifuge apparatus.

The invention provides a centrifuge apparatus for processing blood comprising: an inlet/outlet for blood to be processed and processed components of the blood; a centrifuge separation chamber that is fluidly connected to the inlet/outlet; a container for blood that is fluidly connected to the inlet/outlet; a plurality of containers for receiving separated components of the blood that are fluidly connected to the inlet/outlet; two visible light emitters having different wavelengths and a first corresponding receiver that receives light from both visible light emitters; an infrared light emitter and a second corresponding receiver that receives light from the infrared light emitter; a processor that detects signals from the two corresponding receivers and sends a signal to a control device that switches the output of the inlet/outlet between the plurality of containers for receiving separated components of the blood.

Figure 2A:
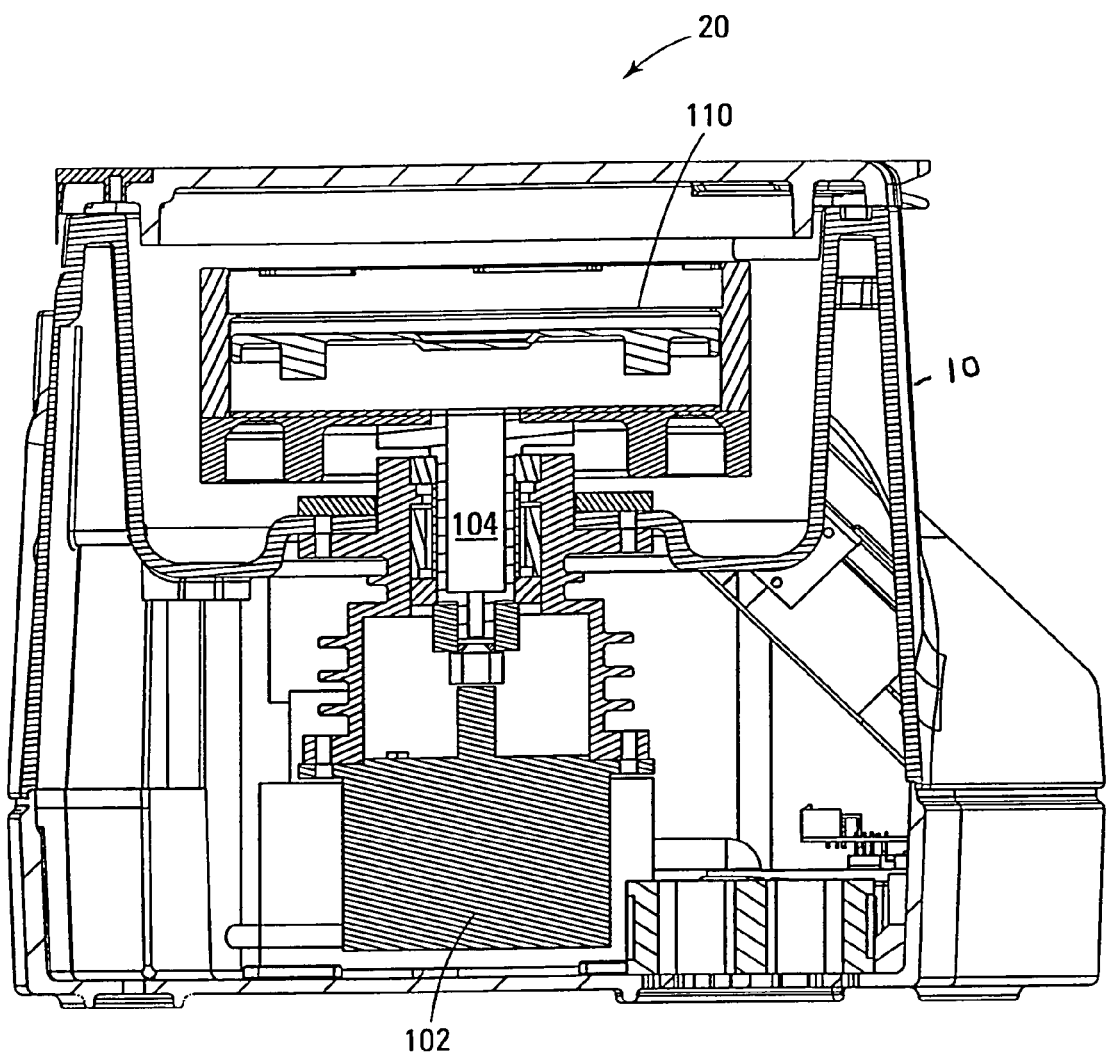
FIGS. 2A and 2B are cross-sectional views of the centrifuge and FIG. 2C is a cross-sectional view of an alternate centrifuge.
Figure 2B:
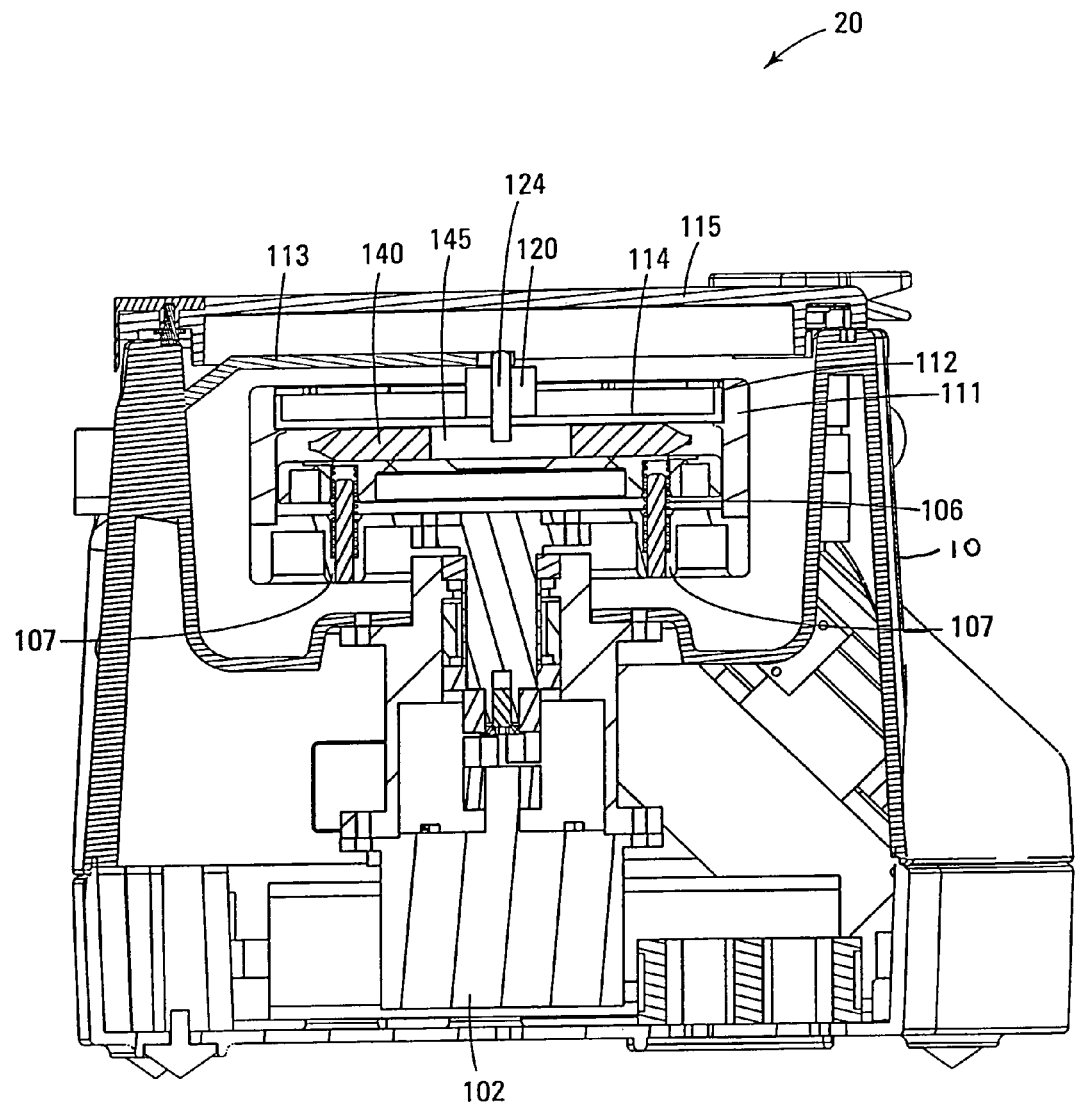

The blood component separation apparatus, as shown and described in the Figures, includes housing 10 containing centrifuge 20 (shown in cross section in FIGS. 2A and 2B). With reference to FIG. 1, the apparatus includes a user interface that comprises touch screen display 30. A single power supply is used for the centrifuge motor, actuators, and for the electronics. The apparatus also includes a fluid sensor 60, 4-way valve 70, and 3-compartment reservoir/collection bag 90. The fluid sensor pathway 60 and the 4-way valve 70 are contained within cartridge 80, which in a preferred embodiment has a snap-on feature so that it is readily removable and maintains its position on the apparatus during use. Blood and its components flow to and from the 3-compartment reservoir/collection bag by means of flexible tubing. A syringe chiller 85 may be provided to keep various fluids in a syringe at a desired temperature. For example, a Peltier device can be used to cool or heat the syringe.

Figure 11A:
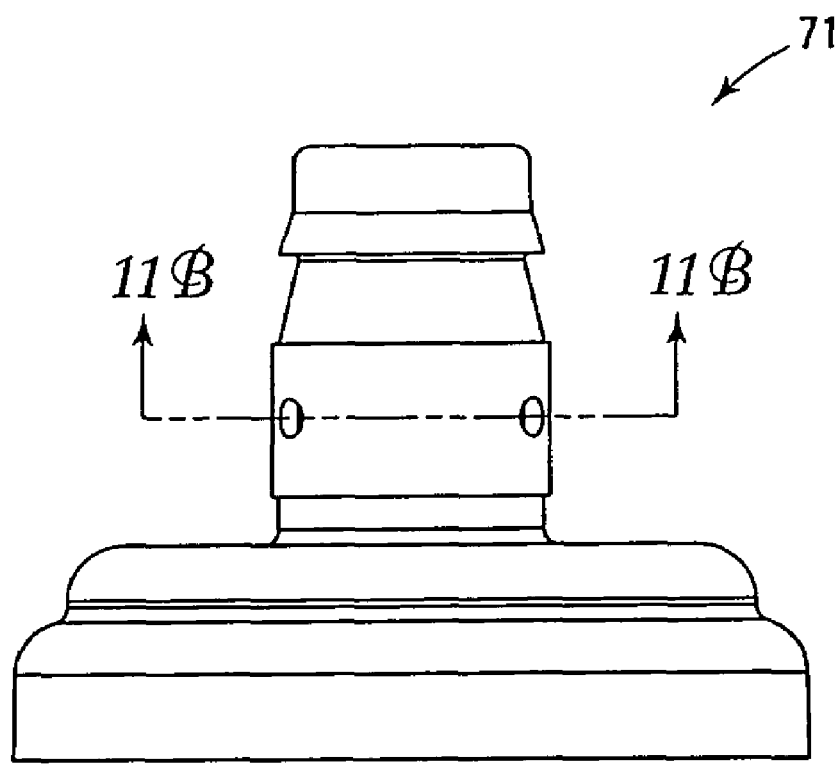
FIGS. 11A and 11B are cross-sectional and side views, respectively, of the valve core.
Figure 11B:
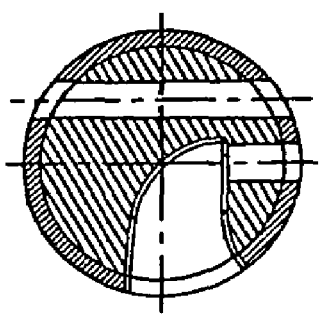

Blood is withdrawn from a patient, mixed with an appropriate anticoagulant (ACD-A, CPD-A) and placed in compartment 906 of the 3-compartment reservoir/collection bag 90, as illustrated in FIG. 1. The bag is connected via tubing line 416 to the 4-way valve core 71 contained within the disposable cartridge 80 (FIGS. 11A and 11B). The disposable cartridge includes a tubing loop 411, which is configured to fit within the raceway of the peristaltic pump 40 contained on the top surface of the housing. One end of the tubing connects to an inlet of a flexible and variable volume separation chamber. The blood is pumped into the centrifuge, where, in the flexible separation chamber, it is separated into concentrated red blood cells (RBC), platelet poor plasma (PPP) and platelet rich plasma (PRP). These components are then transferred out of the flexible separation chamber via tubing lines 410 and 411. The RBC component is transferred to compartment 904 via tubing line 414, and PPP flows into compartment 902 via tubing line 412. The platelet rich plasma (PRP) flows into a syringe via port 802 (syringe not seen in FIG. 1).

The flexible variable volume separation chamber 140 and top support plate 114 fits within the spring loaded plate 110 and top 111, having locking feature 112, on the centrifuge assembly 20. A stator arm assembly 113 engages rotating seal 120. A spring-loaded support plate 110 presses upward against the variable volume separation chamber 140 though it is to be understood that the chamber and holder could be configured so that movement of the plate could be in any desired direction. Motion of the plate, rotation of the peristaltic pump, specified whole blood volume and reduced rotational speed causes expulsion of blood components. These components can exit the port 124 coincident with the axis of the rotating seal assembly 120. A lid 115 covers the centrifuge.

The valve system coupled with optical sensors permits the automation of this process. The graphical user interface (GUI) is object oriented and uses a unified modeling language. The apparatus thus can be used by operators who have varying levels of sophistication.

Centrifuge

In operation, whole blood from the 3-compartment reservoir 90, specifically compartment 906 is pumped through the valve into a variable volume separation chamber 140. The centrifuge is then rotated to separate the blood components. The heavier components migrate to the outer portions of the separation chamber while the lighter components remain near the center of the separation chamber. Centrifuge 20 is shown in cross section in FIGS. 2A and 2B.

Motor 102 is operably connected to hollow shaft 104 which is integrally formed with or mounted on spring-loaded support plate 110. Coil springs 106 comprise one or more springs fit onto shafts 107 and are operably connected to support plate 110. Rotating seal assembly 120 includes port 124. In FIG. 3B, lip-seals 301 attached to center hub 300 seal against a stationary disk 302 which forms a fluid seal. Port 124 provides a passageway to the variable volume separation chamber 140, which is held in the space between rigid support plate 114 and spring loaded plate 110. Motor 102 rotates spring loaded plate 110, rigid support plate 114, and variable volume separation chamber 140.

During centrifugation, lower density blood components accumulate in the center region 145 of separation chamber 140, that is, close to the axis of rotation, while higher density components are urged toward the outermost region. The bottom support plate 110 moves down to accommodate the blood components due to centrifugal force.

For example, once whole blood has filled the separation chamber in the centrifuge, the centrifuge is run for 7 minutes at 4000 rpm. Then the rotation of the centrifuge motor is decreased. Decreasing the speed of the centrifuge causes reduced pressure inside the bag, allowing the spring-loaded support plate 110 to move upward against flexible reservoir 140, causing its contents to be expelled via port 124. This, along with operation of peristaltic pump 40 in a direction reverse to that during which the variable volume separation chamber was filled, causes expulsion of the blood components through the fluid exit port coincident with the axis of the centrifuge (i.e., port 124).

Because PPP is less dense, it is expelled first. The PPP is directed through tubing 410 to the valve system, and fed into the PPP compartment of the 3-chamber reservoir bag, as described below for FIGS. 7 to 10. Other components follow in sequence, also as described further below.

Figure 2C:
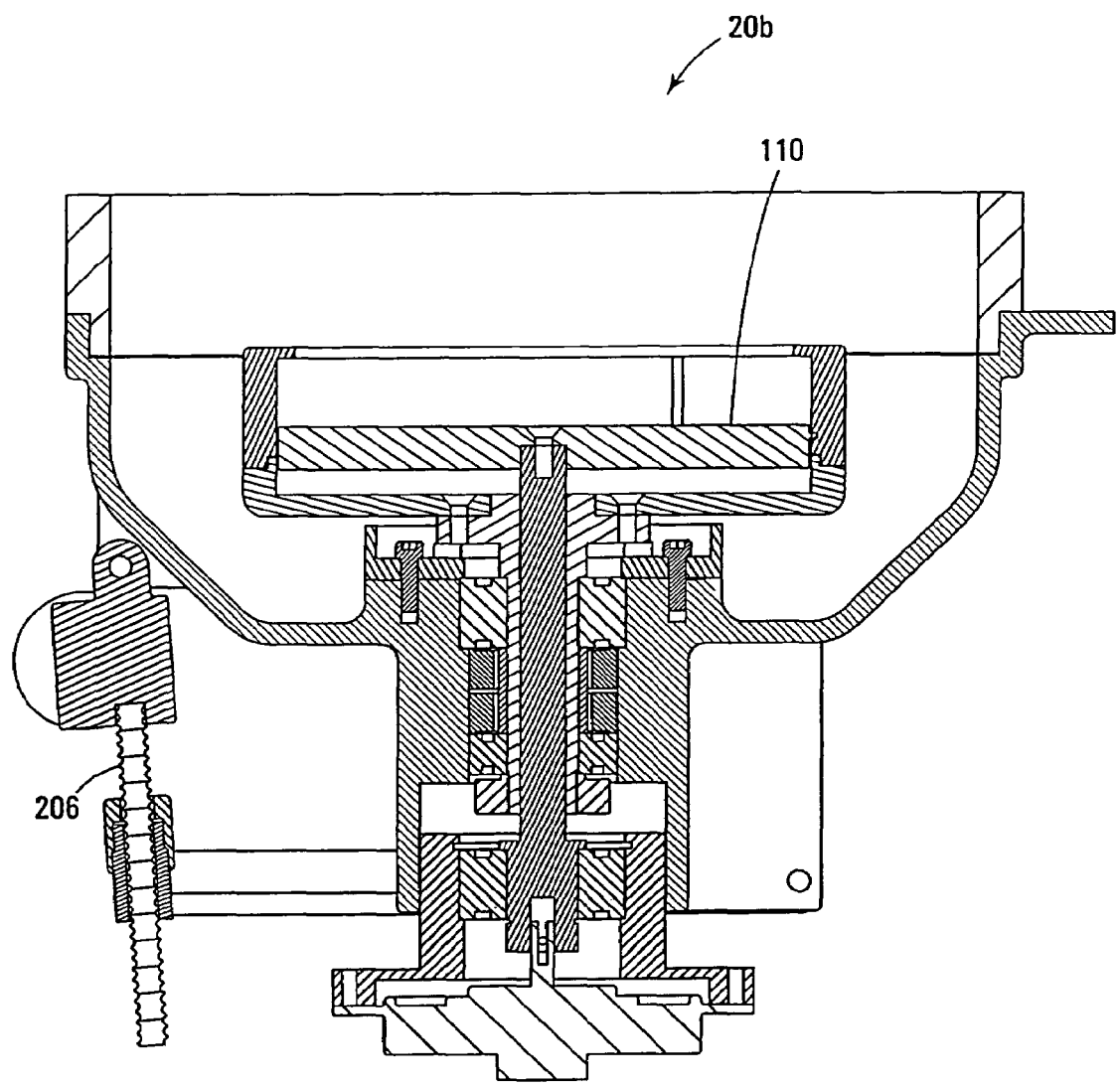

FIG. 2C illustrates an alternate embodiment of the centrifuge, and shows centrifuge 20b in a cross-sectional view wherein ball-screw actuator 206 is used to control the space between the top holder and the bottom plate. The ball-screw actuator 206 as an example is automatically controlled to maintain the desired space between the top holder 114 and the bottom plate 110. It is possible to use other mechanical means such as pneumatic, hydraulic or other mechanical actuators to achieve desired positioning of the bottom plate. Use of a pump to move fluids could be eliminated with a mechanical actuator. Such an actuated bottom plate could draw fluids in and expel fluids from the separation chamber.

Figure 18:
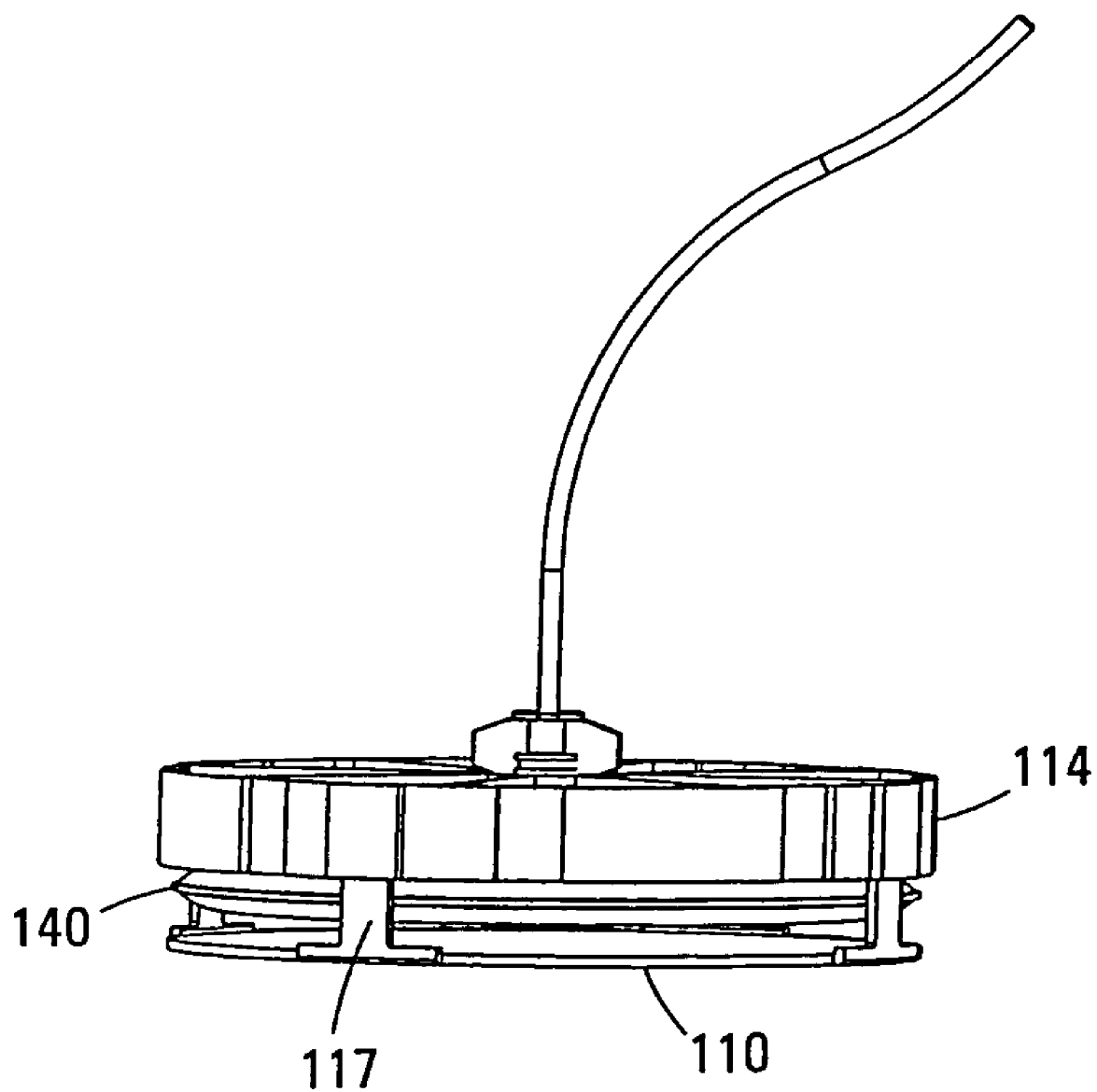
FIG. 18 is a perspective view of a flexible disk bag mounted in a centrifuge between the top plate and the bottom plate.

Typically the apparatus of this alternate embodiment invention will be used by placing whole blood in the 3-chamber reservoir bag and transferring it from there to the centrifuge. However, it is possible to collect blood directly from the patient in the flexible disk bag of the centrifuge. The flexible disk bag is the preferred embodiment of the variable volume separation chamber. Since it is necessary to mix the collected blood with an anti-coagulant, it is important to know the amount of blood being processed. The flexible disk bag is mounted in the centrifuge between the top plate and the bottom plate. The distance between the top plate and the bottom plate correlates to a known volume of blood in the flexible disk bag as shown by a graduated scale 117 (shown in FIG. 18), which the user can visually inspect to determine the amount of blood entering the flexible reservoir. The operator thus can monitor the amount of anti-coagulant and whole blood collected without the use of a separate scale.

Figure 3A:
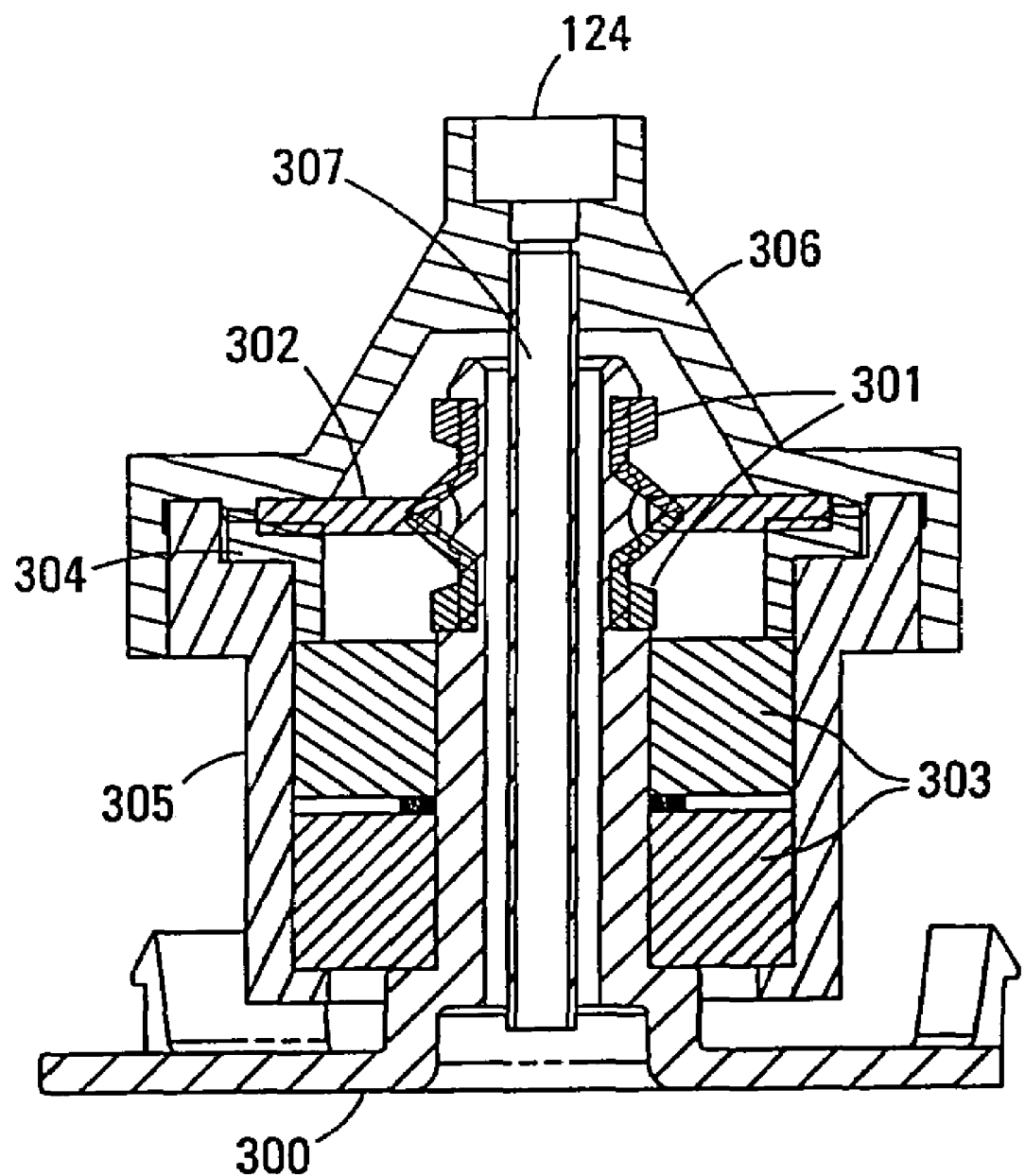
FIGS. 3A to 3D are cross sectional views of the rotating seal of the centrifuge.
Figure 3B:
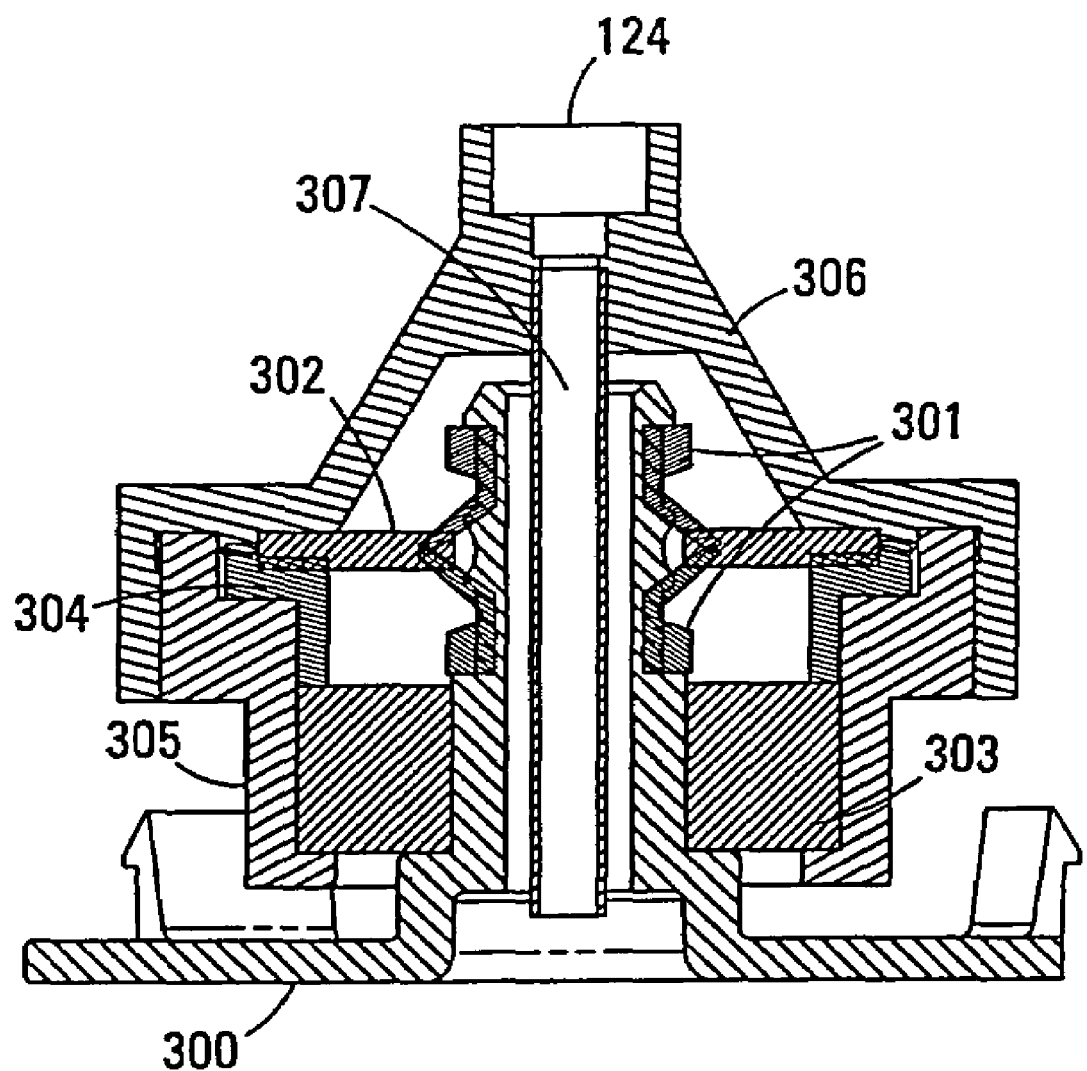
Figure 3C:
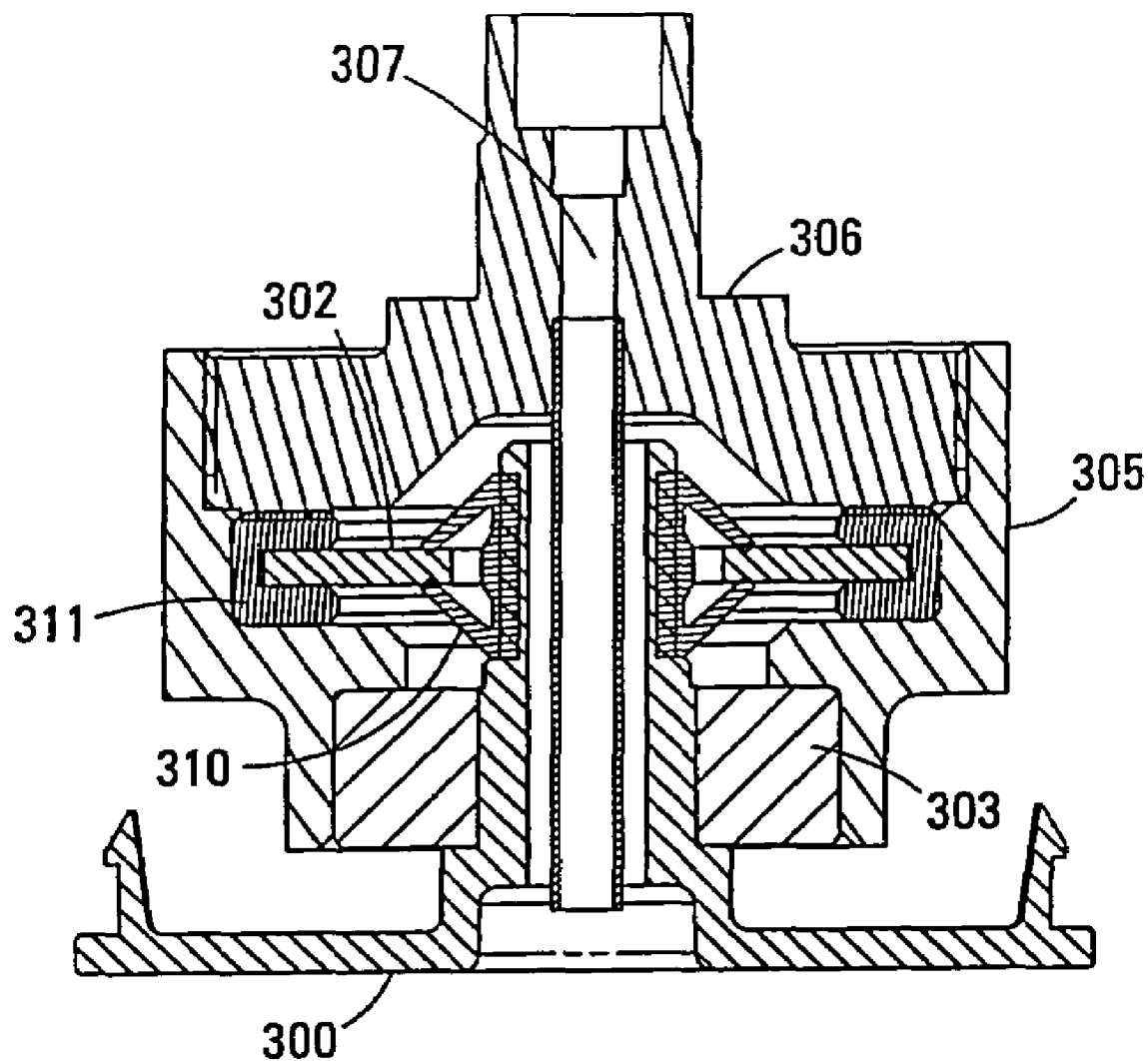

FIGS. 3A to 3C show various embodiments of a rotating seal. The rotating seal shown in FIG. 3A is equivalent to the one shown in FIG. 3B. The only difference in the designs is the presence of two bearings 303 in FIG. 3A versus one bearing in FIG. 3B. Two bearings provide greater stability of rotating components. FIGS. 3A and 3B both have a center hub 300 that is attached to the center axis of the separation chamber 140. Bearing 303 is press fit onto the shaft of the center hub 300. Flexible lip-seals 301 are attached to the center hub 300 and create a fluid seal with a stationary sealing disk 302. Disk 302 is centered and sealed by a compressible gasket 304 that also provides a pre-load to the outer race of the bearing 303 when compressed. The lower housing 305 provides features that contain the above mentioned components. Top housing 306 is attached to the lower housing 305 and compresses and seals the internal components of the rotating seal. Prior to assembly the center tube 307 is attached to the upper housing either by press fit, insert molding or molded. The center tube allows for the transfer of fluid in and out of the device. The rotating components of this design are the separation chamber 140, the center hub 300, and the lip seals 301. All other components are held stationary during centrifugation. The rotating lip-seal 301 interface to stationary disk 302 creates a positive and negative pressure fluid seal.

FIG. 3C is similar to FIGS. 3A and 3B. The design shown in FIG. 3C differs with a press fit bearing 303 into the lower housing 305, a one piece lip seal 310 versus two lip seals and a flexible gasket 311 that seals the outer edge of the sealing disk 302. The upper housing 306 is attached to the lower housing 305 and compresses gasket 311.

Figure 3D:
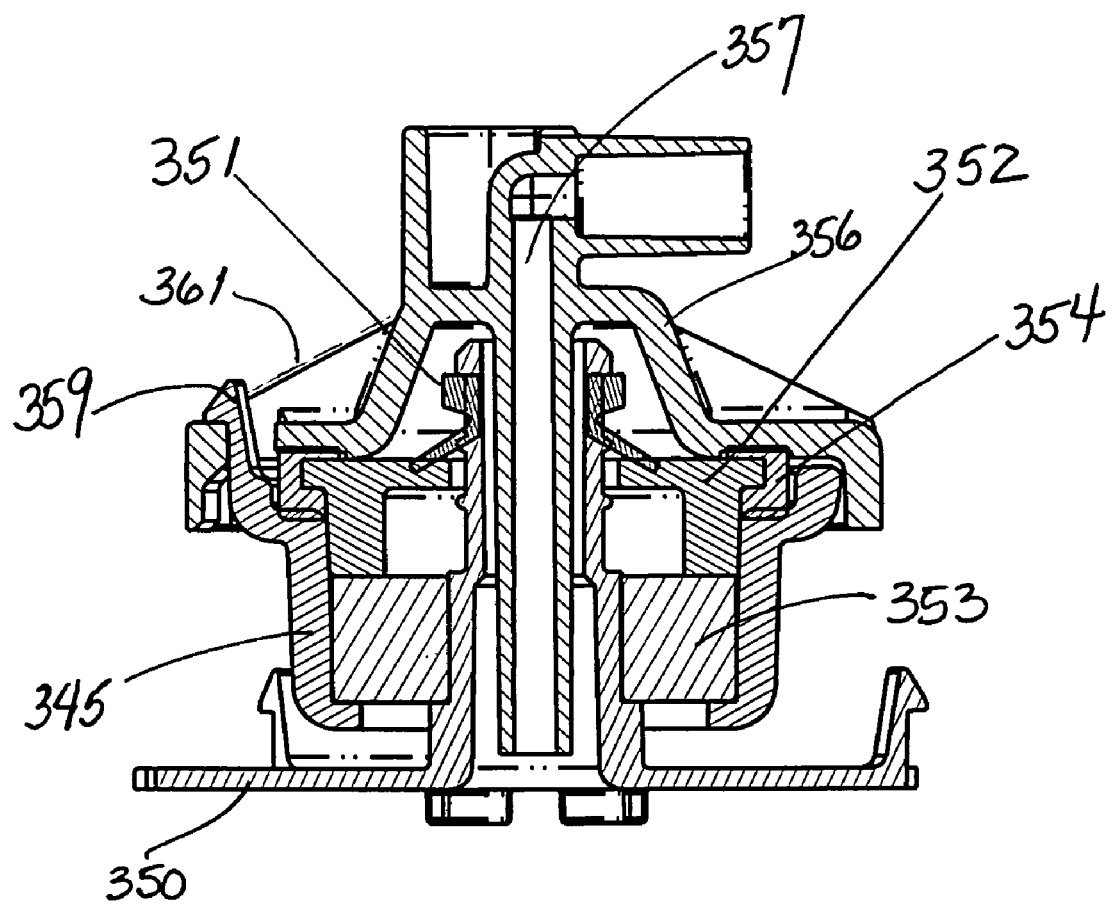

FIG. 3D shows another embodiment of a rotating seal. Center hub 350 is attached to the center axis of the separation chamber 140 (FIG. 2B). Bearing 353 is press fit onto the shaft of the center hub 350. Flexible lip-seals 351 are attached to the center hub 350 and create a fluid seal with a stationary sealing disk 352. The stationary sealing disk may comprise stainless steel or a ceramic. Disk 352 is centered and sealed by a compressible gasket 354, which extends around and over disk 352 to provide additional sealing, as compared to, for example, gasket 304 in FIG. 3B. Lower housing 345 additionally is provided with snap fit component 359, configured to engage top housing 356. Thus top housing 356 compresses and seals the internal components of the rotating seal. Top housing 356 is provided with optional ribs 361 which provide support for the housing.

Center tube 357 may be molded, press fit, or otherwise attached to the upper housing 356. The center tube allows for the transfer of fluid in and out of the device. The rotating components of this design are the separation chamber 140, the center hub 350, and the lip seals 351. All other components are held stationary during centrifugation. The rotating lip-seal 351 interfaces to stationary disk 352 and creates a positive and negative pressure fluid seal.

Figure 4B:
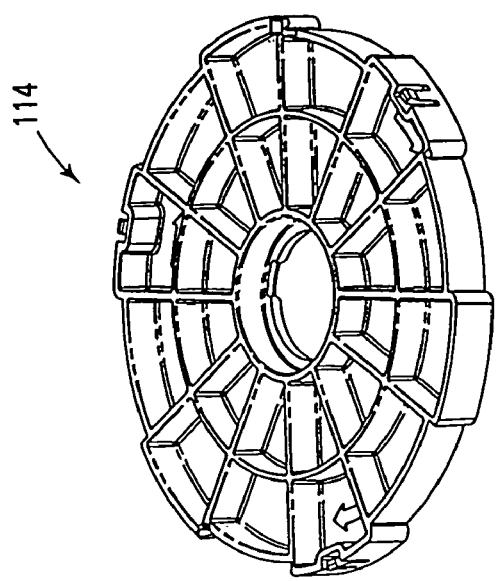
FIGS. 4A to 4C are top, perspective and side views, respectively, of rigid support plate used in the centrifuge of FIGS. 2 and 3
Figure 4A:
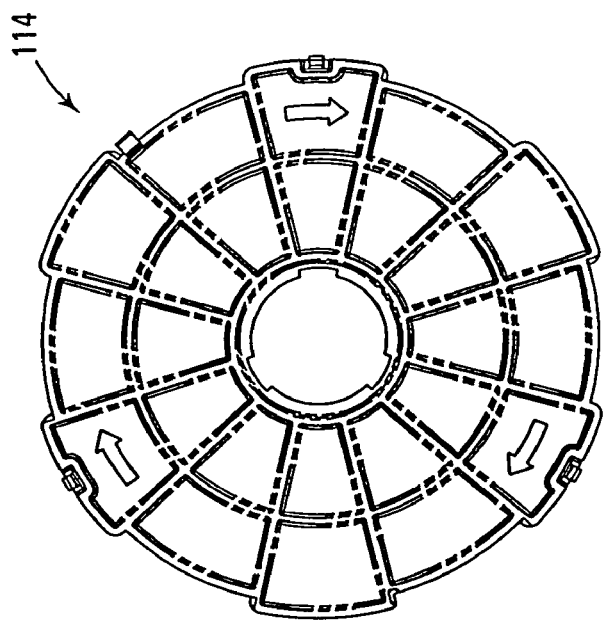
Figure 4C:
Figure 4D:
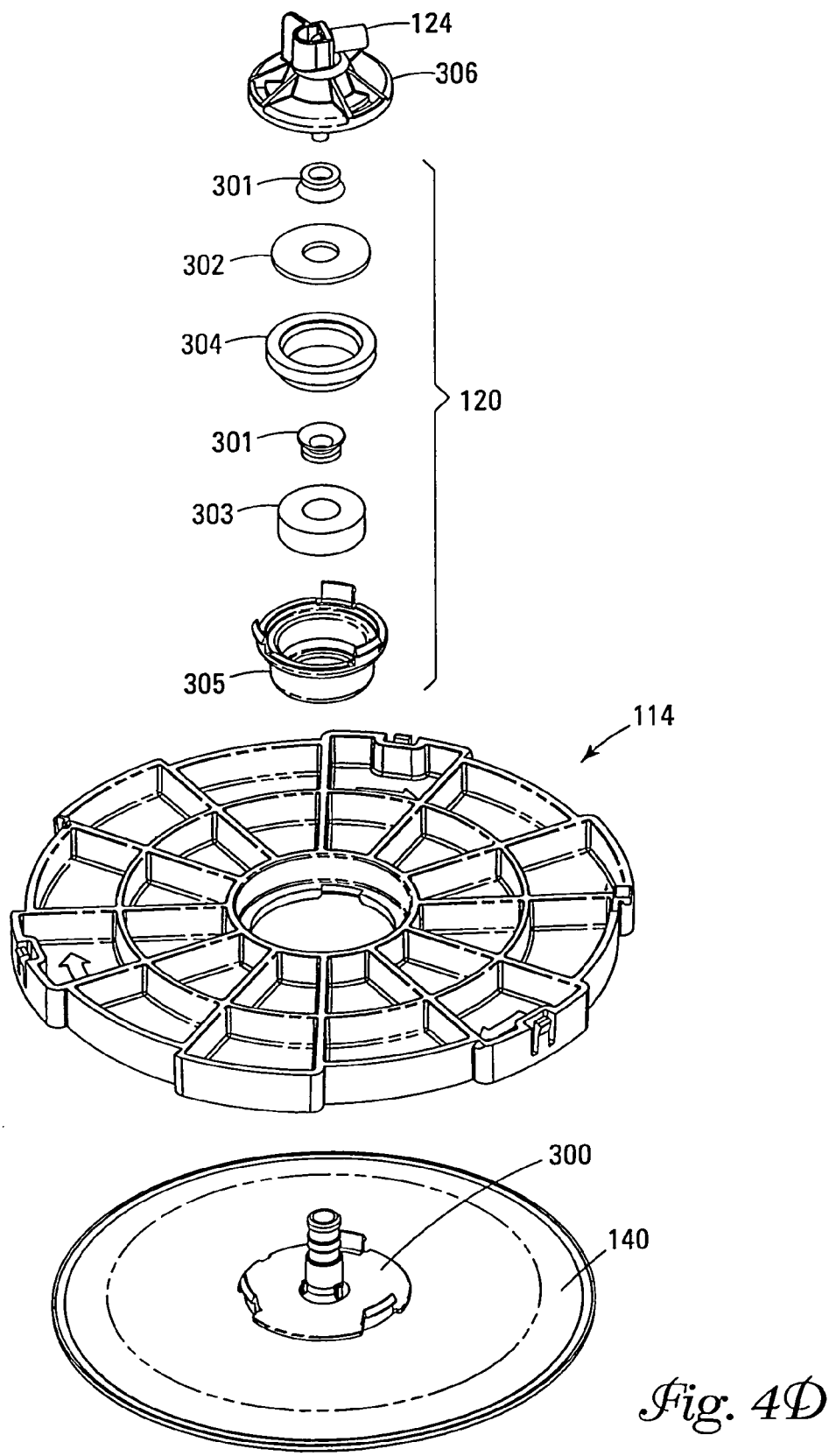
FIG. 4D is an exploded view of the top support plate, port, and rotating seal assembly.

FIGS. 4A to 4C show various views of the top support plate 114. The top support plate is designed to provide structural support for the expanding variable volume separation chamber. FIG. 4D illustrates an exploded view of the separation chamber assembly, showing the top support plate 114, port 124, rotating seal assembly 120, center hub 300 and variable volume separation chamber 140. The rotating union generated by the rotating seal assembly 120 allows fluid to enter and exit the variable volume separation chamber while the chamber is rotating.

PRP Sequestration

Platelet collection can be optimized by automatically adjusting system parameters based on processing volumes. These parameters include spin speed (i.e., rpm) and spin time.

A cycle is the process of filling the separation chamber with whole blood (Fill), spinning the blood to separate the components (Spin), and emptying the separation chamber by depositing separated cells in their appropriate compartments (3-compartment reservoir) and into the PRP syringe.

PRP product is the PRP automatically deposited in the PRP syringe during a cycle plus the volume of PPP pulled into the PRP syringe at the end of a cycle.

The equations that define the processing parameters are:

Volumes of 30 to 89 mL:
1) rpm1=3500
2) time1=0.0011 $(Vol)^2$−0.067(Vol)+3.0
3) rpm2=3000
4) time 2=−0.0011$(Vol)^2$+0.08(Vol)+7.7

Volumes of 90 to 119 mL:
1) rpm1=16.67(Vol)+2000
2) time1=0.17 (Vol)−9.32
3) rpm2=3000
4) time2=−0.133 $(Vol)^2$+17.96

Volumes of 120 to 180 mL:
1) rpm1=4000
2) time1=11
3) rpm2=3000
4) time2=2

Hematocrit Function

The hematocrit function RBC (vol.) is defined by equations that describe the volume of additional red blood cells added to the PRP product syringe during a processing cycle. This variable is selected and adjusted by the clinician on the user interface and directly affects the final hematocrit of the PRP product. The PRP product hematocrit is the percentage (based on volume) of red blood cells in the total PRP product volume.

The final PRP product consists of the PRP volume automatically deposited in the PRP syringe during a cycle, plus the volume of PPP manually drawn back into the PRP syringe from the PPP compartment 902 at the end of the processing cycle.

The equations that define the red cell volume function are:
RBC (vol.)=(m*h(Processing Volume)+(b*h))*(0.95/1.05)
h=desired hematocrit in 10% PRP product
m=(−3.4e−05)h+0.00184
b=−0.00158h+0.075

Graphical User Interface

Housing 10 includes a user interface comprising touch screen display 30, a stop button 301, a power switch, and various connectors for external electrical interface. The touch screen is resistive so that it will function if the operator is wearing gloves. The stop button is used to interfere with automatic operation if the operator deems necessary. Processing of blood using a fully automatic or manual collection of blood components can be achieved from this user interface. Manual collection provides the clinician with a selection of valve buttons on the user interface that allow the clinician to direct the blood components to the desired collection vessel. All other operator interfacing is accomplished from this one screen using 3-D appearance of control features and judicious use of color. The external interfaces are used to upgrade software, download data, and possibly connect to a printer.

Cartridge

Figure 5A:
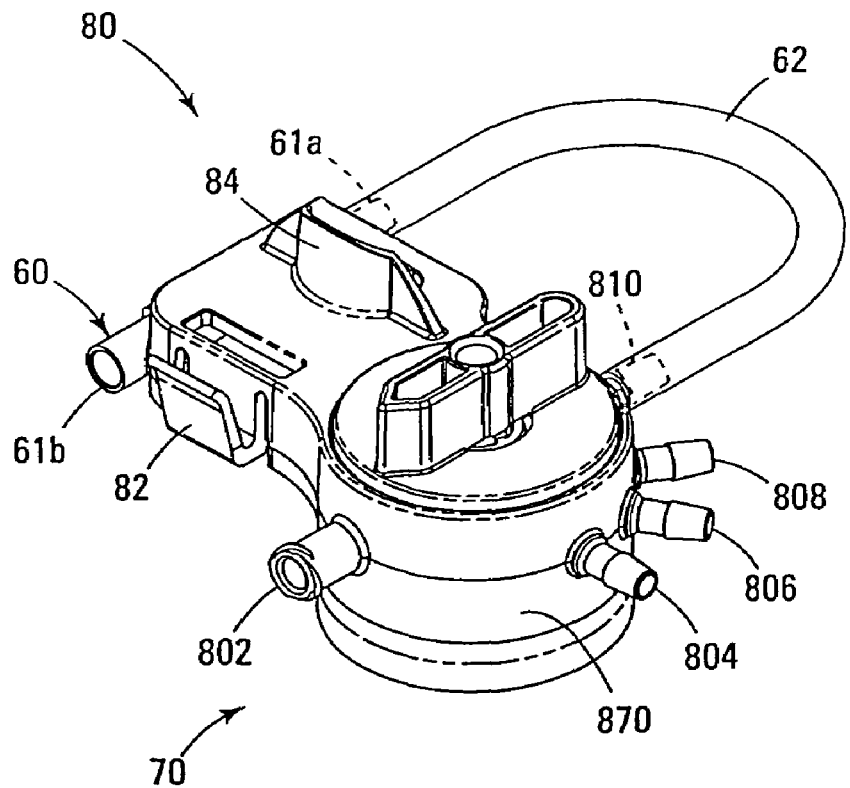
FIG. 5A is a perspective view and FIG. 5B is a side view of the cartridge that contains the fluid sensor and the valve assembly.
Figure 5B:
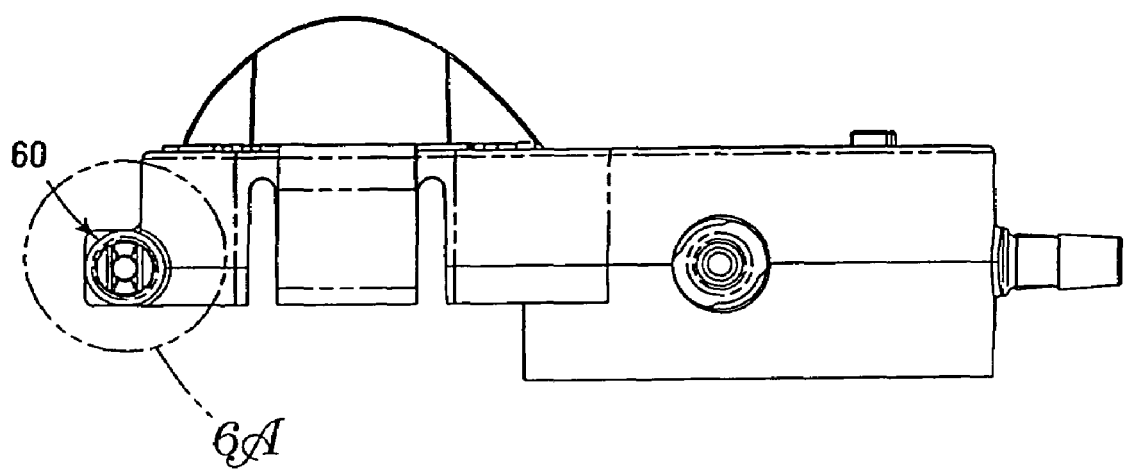

FIG. 5A shows cartridge 80 that contains fluid sensor pathway 60 and the valve assembly 70. Cartridge 80 typically comprises injection molded polymer. The cartridge is provided with snap-on features 82 and 84 that permit easy removal of the cartridge from the apparatus. (Snap tab 890 is shown in greater detail in FIG. 13.) Valve housing 870 contains ports 802, 804, 806, 808, and 810, each of which connect to tubing lines for the transfer of fluid to and from the centrifuge to the 3-compartment reservoir and/or to a syringe. Cartridge 80 also includes fluid sensor pathway 60. Tubing 62 connects port 810 to fluid sensor pathway outlet 61a. Tubing 62 is placed in the raceway of the peristaltic pump. Blood flows in and out of fluid sensor pathway 60 through outlets 61a and 61b.

Figure 6B:
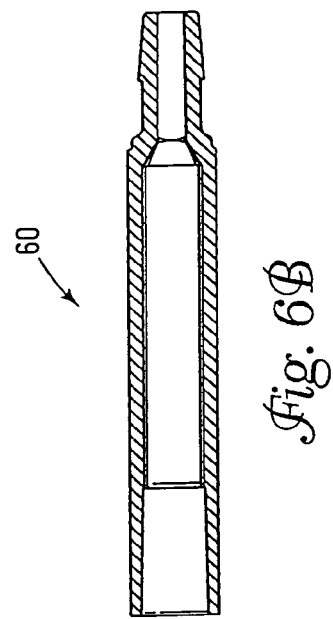
FIG. 6A is a side view and FIGS. 6B and 6C are cross-sectional views of the fluid sensor pathway.
Figure 6C:
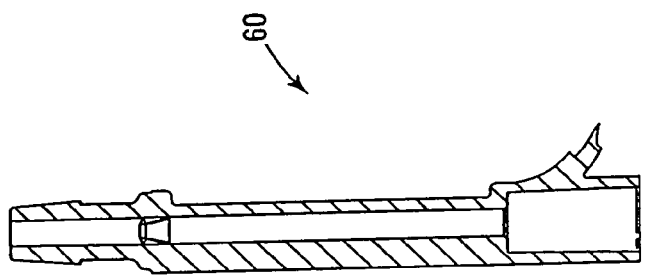
Figure 6A:
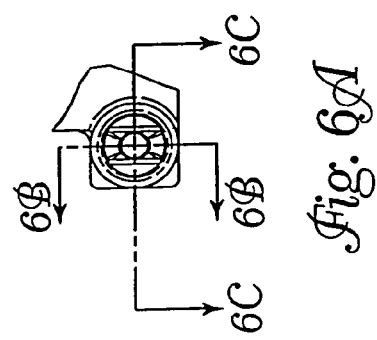

FIGS. 6A to 6C illustrate the section views of the fluid pathway geometry for the fluid sensor. FIG. 6B provides a side section view of the fluid sensor pathway in which the fluid flow is thinned out to allow improved detection of whole blood component layers.

Sensors

Blood components flow through the fluid sensor pathway 60 and the flow is monitored at various wavelengths. An algorithm is used to determine what component layer is in the fluid sensor pathway: RBC, PPP, PRP, or air. A combination of absorption and scattering causes the signal to change. Computer software controls the intensity of the LEDs. A cutaway view of the photodiode detector placement is shown in FIG. 12. Photodiode detectors are configured to fit in pockets or openings 510 and 512. These pockets are adjacent to fluid sensor pathway 60.

Sensing System

Red blood cells absorb electromagnetic radiation to different degrees dependent on wavelength. Platelets do not absorb light. Because scattering is due to a localized change in the index of refraction of a medium, both red blood cells and platelets will scatter light. The shorter the incident wavelength the greater the scatter from red blood cells or platelets.

Away from a scattering site, the index of refraction is that of the plasma. As light passes through plasma containing only a single red blood cell, some light will be scattered. When a second red blood cell is added, a greater percentage of light will scatter. The maximum scatter occurs when half the volume has an index of refraction of plasma, and half has an index of refraction of the red blood cell. As the hematocrit (hct) increases above 50%, the scattering effect will again decrease.

The sensing system of this invention uses the absorption and scattering characteristics of red blood cells and platelets at different wavelengths to determine when there is a transition from one component to the next as the centrifuge chamber is emptied. The sensor also detects the transition from air (or the absence of any blood component) to either whole blood (while filling the centrifuge) or to PPP (while emptying the centrifuge.)

The sensing system comprises three LEDs (light emitting diodes) and two photodiode light detectors. The three LEDs have wavelengths of 470 nm, 940 nm, and 1300 nm. The light generated by the 470 nm and the 940 nm LEDs is detected by one of the detectors/photodiodes, while light generated by the 1300 nm LED is detected by the other photodiode. Because the detector/photodiode sensing the 470 nm and 940 nm light is also sensitive to room light, Time Division Multiplexing is utilized with the LED signals, with a time window dedicated to all LEDs off. In this method, the light emitted from each LED is electronically chopped by pulsing the LEDs on and off in sequence. The detector/photodiode response is then sampled so that any signal due to the ambient background light can be canceled out.

Blood flows through a transparent chamber (preferably comprising polycarbonate) having a near-elliptical cross section. LEDs are positioned so that light travels perpendicular to the path of the blood flow. The sides of the chamber through which light passes preferably are flat. The second detector/photodiode is more responsive to the 940 nm light. Accordingly, the 470 nm LED is set so that it shines directly at the detector, while the 940 nm LED is positioned off-center.

Because absorption and scattering characteristics are functions of wavelength, it is preferred to use different wavelengths originating from different LEDs. The use of different wavelengths enables the detection of various blood components. A 470 nm LED provides light having both high intensity and short wavelength. This wavelength will be scattered by both platelets and red blood cells. A wavelength of 470 nm is also strongly absorbed by red blood cells. A wavelength of 940 nm is neither scattered nor absorbed as strongly as a wavelength of 470 nm. The 1300 nm wavelength is not absorbed by the red blood cells and scattering is not as significant as with the shorter wavelengths.

Although both the absorption and the scatter drop off as the wavelength increases, the change is not the same for the two effects. Therefore, the use of three different wavelengths yields a great deal of relevant information.

The intensity of the light emitted from the LEDs is electronically adjustable through a current sensing, voltage feedback amplifier. The signal from the detector is monitored, while the intensity of the light is adjusted, until the signal falls within a pre-defined window. This process is accomplished automatically in software for each new sample. This calibration process does not require an operator.

The intensity of each LED is adjusted and set by software running on a single board computer with a 16 bit data bus. The lower 8 bits are used to adjust the intensity through a Digital to Analog converter. The analog voltage produced at the converter is used to adjust the current through the LED.

The voltage of the "Sensor 470 Intensity" signal ranges from 0 to 5 volts. When the "Sensor 470 Enable" signal is greater than 2.5 volts, the intensity voltage is applied to the non-inverting input of the Op Amp. (When the enable signal is less than 2.5 volts, the non-inverting input of the Op Amp is shorted to ground through the open collector comparator. The enable signal is digital, and is therefore either 0 or 5 volts.) The feedback on the Op Amp is used to apply the same voltage as the intensity signal across the load resistor. Therefore, the current through the LED is equal to the voltage of "Sensor 470 Intensity" divided by the value of the load resistor.

The load resistor is sized to limit the current through the LED to a value that will not cause it damage. The transistor is used in the output circuit of the Op Amp to prevent the Op Amp from having to source all the current for the LED.

When a new disposable set is used, the software adjusts the intensity of the LEDs until the signal at the detector is within a pre-defined window. In this way, the apparatus of this invention compensates for variation in disposables, variation in disposable location, and any aging effect on the LEDs or detector elements. If this automatic calibration fails to adjust the LED intensities to the required value, the machine will not allow operation.

Once the intensity of all three LEDs is set, with the disposable in place, the apparatus can be used to separate the sample of the patient's blood into the desired components. The transmittance of light through the blood is monitored in the disposable whenever the pump is running. The software makes decisions based on the transmittance values, ratios of transmittance values, and the derivatives of these values with respect to time.

The blood components are identified by the intensity of the light transmitted through the blood and by the derivative of the intensity as a function of time. Because the blood is flowing through the sensor while the light intensity is being sampled, the derivative of the intensity is also a function of blood volume passing through the sensor. The components that are identified are (1) whole blood; (2) clean plasma (low platelet count, and low Hct); (3) platelet rich plasma; (4) high Hct plasma; and (5) air.

Valve

The blood is separated into components in the centrifuge, which is connected by tubing to a 4-way valve 70 contained within a disposable cartridge 80 (FIGS. 5 to 11). The disposable cartridge can be snapped onto the housing for ease of removal.

Figure 7A:
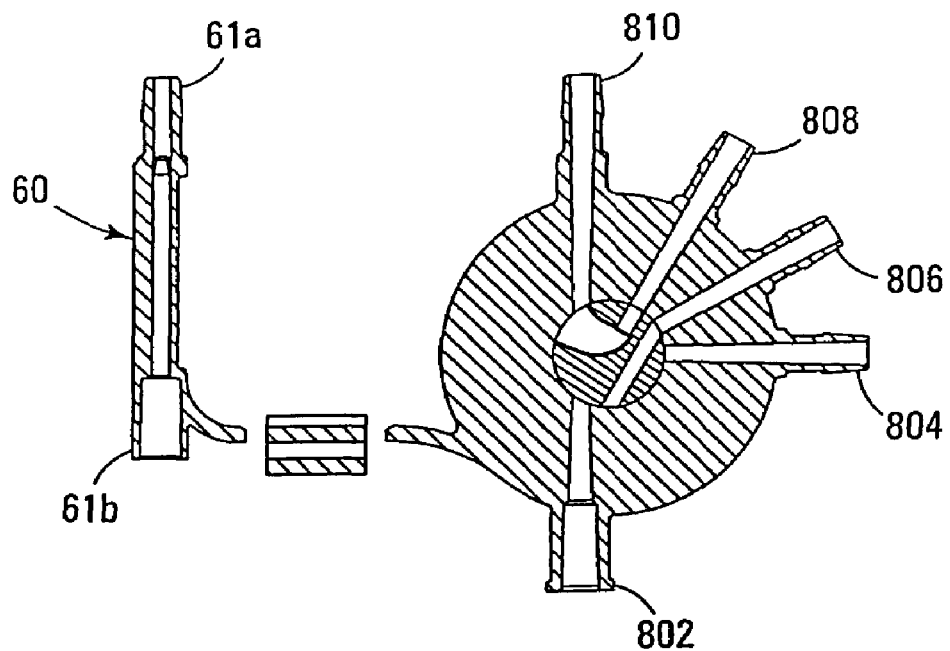
FIGS. 7A and 7B are cross-sectional and side views, respectively, of the valve assembly when whole blood is flowing into the centrifuge.
Figure 7B:
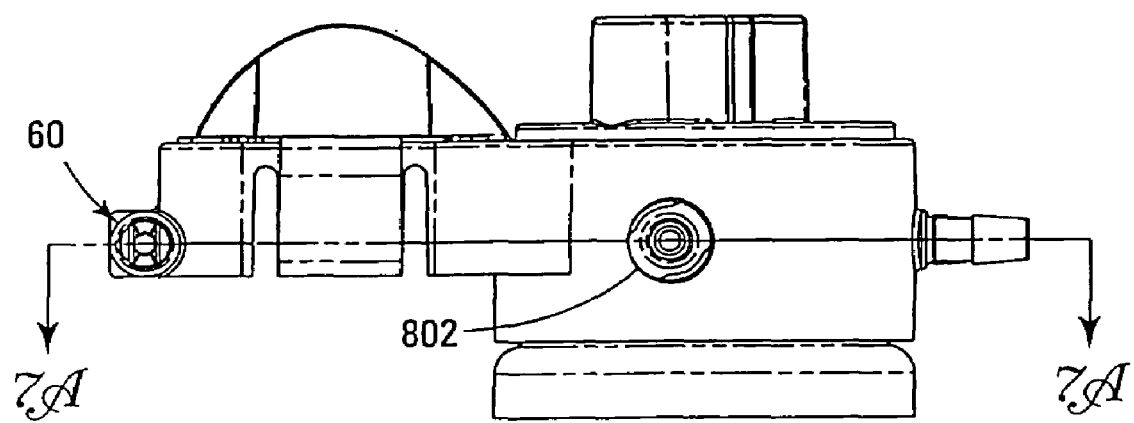
Figure 8A:
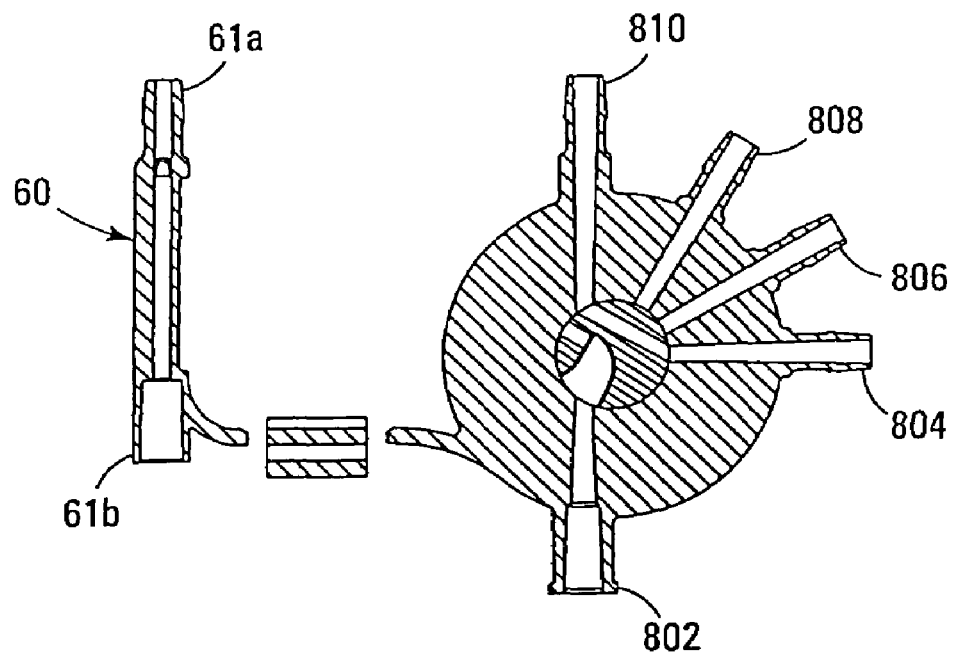
FIGS. 8A and 8B are cross-sectional and side views, respectively, of the valve assembly when PPP is flowing out of the centrifuge.
Figure 8B:
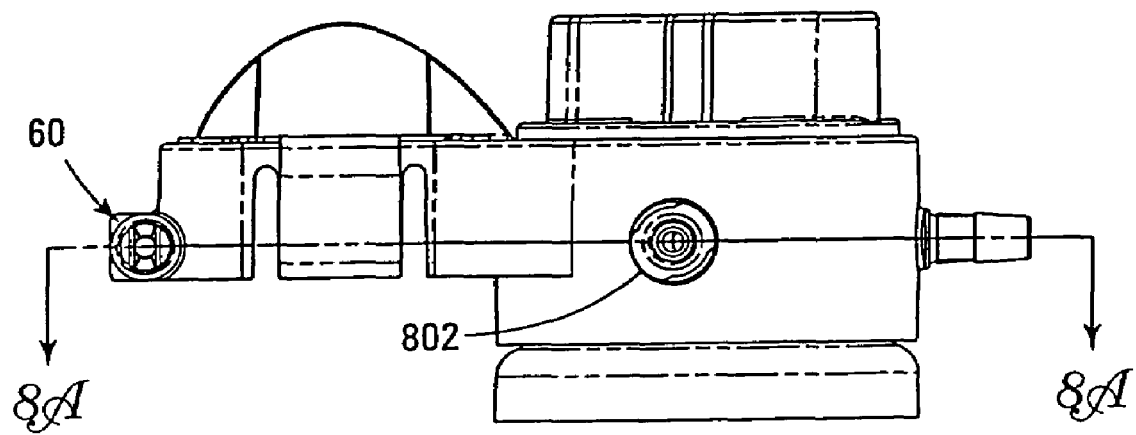
Figure 9A:
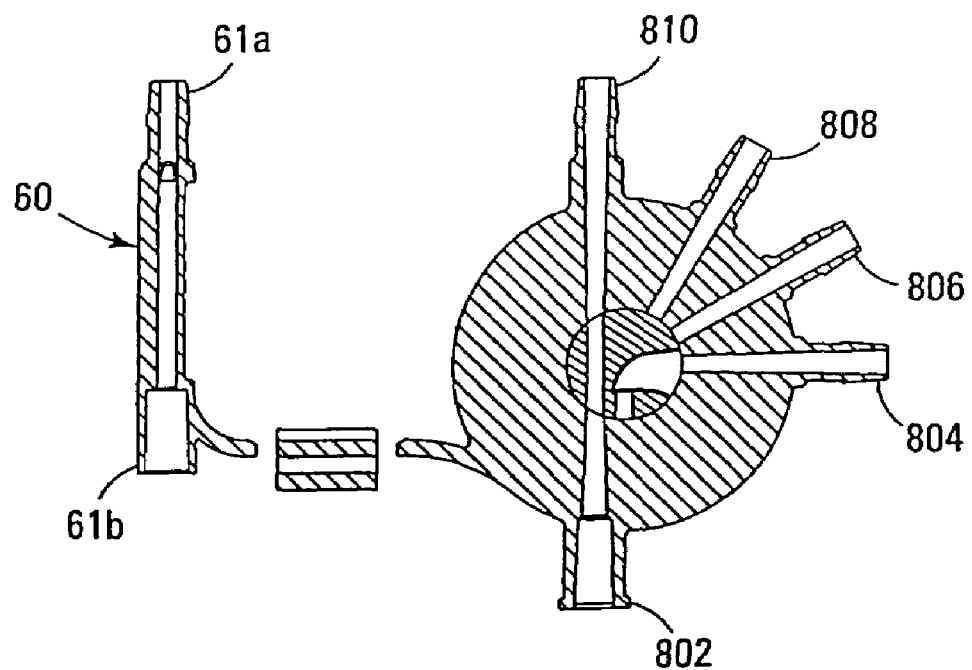
FIGS. 9A and 9B are cross-sectional and side views, respectively, of the valve assembly when platelet rich plasma is flowing out of the centrifuge.
Figure 9B:
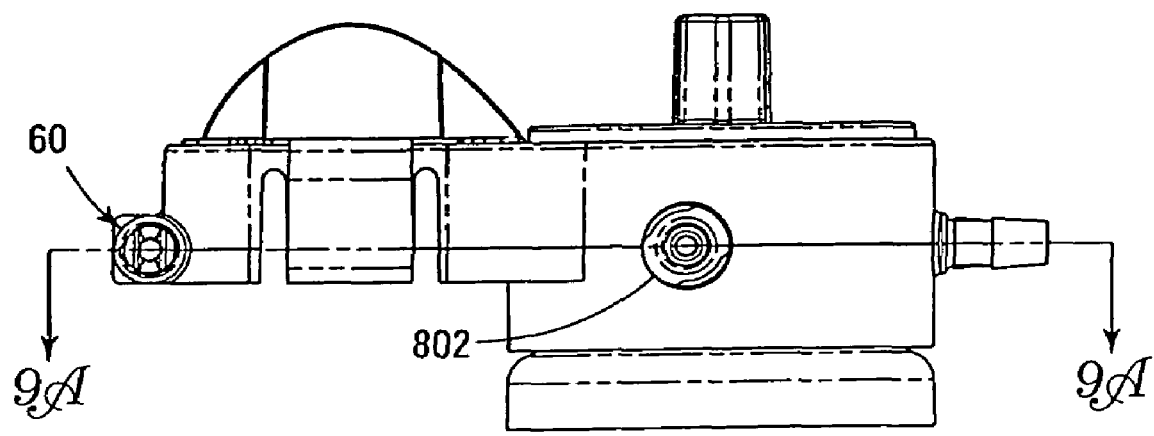
Figure 10A:
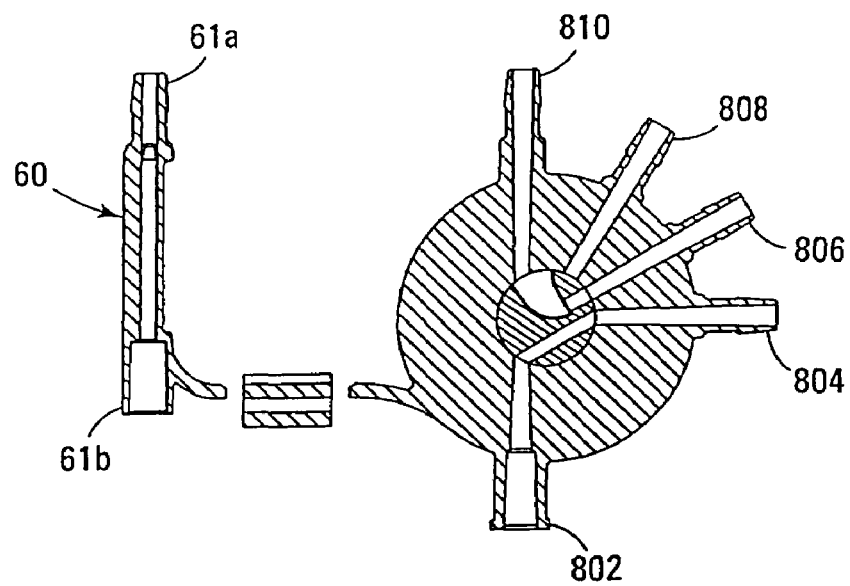
FIGS. 10A and 10B are cross-sectional and side views, respectively, of the valve assembly when RBC and air are flowing out of the centrifuge and into the RBC compartment of the reservoir.
Figure 10B:
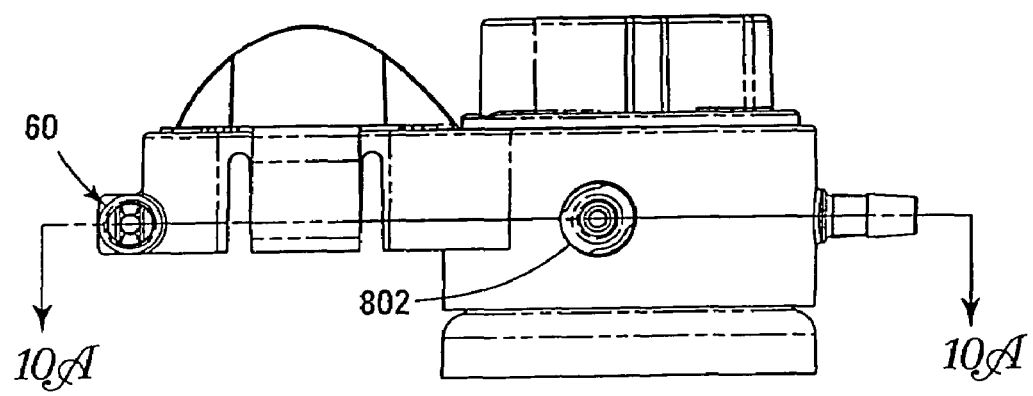

The valve is designed so that whole blood flows through the valve in its "home" position and into the centrifuge, as illustrated in FIGS. 7A and 7B. The valve is then rotated to the position shown in FIG. 10A to allow the pump to pump air through the tubing to displace the residual whole blood volume into the centrifuge. After centrifugation of the whole blood, the valve moves to provide a path for the platelet poor plasma (PPP) to exit the centrifuge (FIGS. 8A and 8B). The valve then moves so that platelet rich plasma (PRP) can flow from the centrifuge into the collection bag (FIGS. 9A and 9B). In FIGS. 10A and 10B, red blood cells (RBC) exit the centrifuge. Also in this position while red blood cells are being pumped from the separation chamber, platelet poor plasma (PPP) can be aspirated back to be mixed with platelet rich plasma (PRP) to dilute the PRP, if desired.

FIGS. 11A and 11B show the 4-way valve core 70. A stepper motor drives the valve core 70 to the desired locations during processing. There is a potentiometer to verify valve position based on voltage. Voltages and current are measured for diagnostic purposes.

Reservoir/collection Bag

FIG. 14 shows an embodiment of 3-compartment reservoir bag 90. The bag is flexible and preferably comprises a PVC polymer. Preferably the bag is transparent so that fluid levels can be seen easily. Whole blood is placed into compartment 906. The blood is pumped out of this compartment (by peristaltic pump 40) and into the variable volume separation chamber 140 of the centrifuge. Reservoir/collection bag 90 is shown as a 3-compartment unit, and it is to be understood that this bag could be perforated for easy separation of the compartments.

After centrifugation, the blood components are sent from the centrifuge through tubing line 410 through peristaltic pump 40 via tubing line 411 into valve 70 and thus to the separation/collection bag via tubing lines 412, 414, and 416. See FIG. 1. A preferred embodiment of the bag is shown in FIG. 14, wherein PPP is in compartment 902, RBC is in compartment 904, and whole blood is in compartment 906. Compartments 902 and 904 are provided with outlets 912 and 914 so that the contents can be completely and easily removed, typically by syringe. Compartment 906 is provided with inlet 913. In addition, compartments 902, 904 and 906 are provided with vents 924 and 926 to allow air to enter and exit.

Alternate Embodiments

Figure 15:
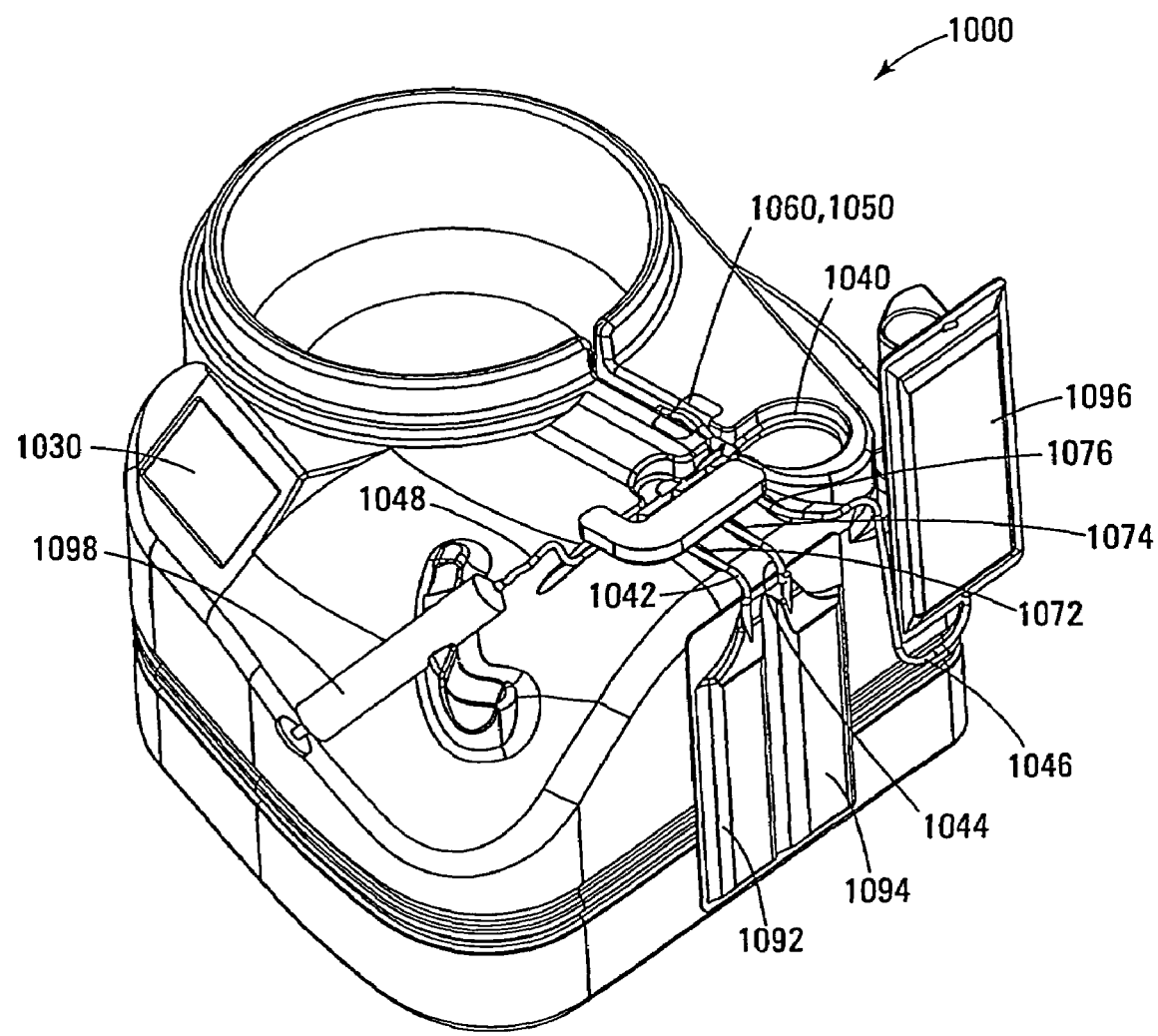
FIG. 15 is a perspective view of an alternate embodiment of the apparatus of this invention.
Figures 16A, 16B:
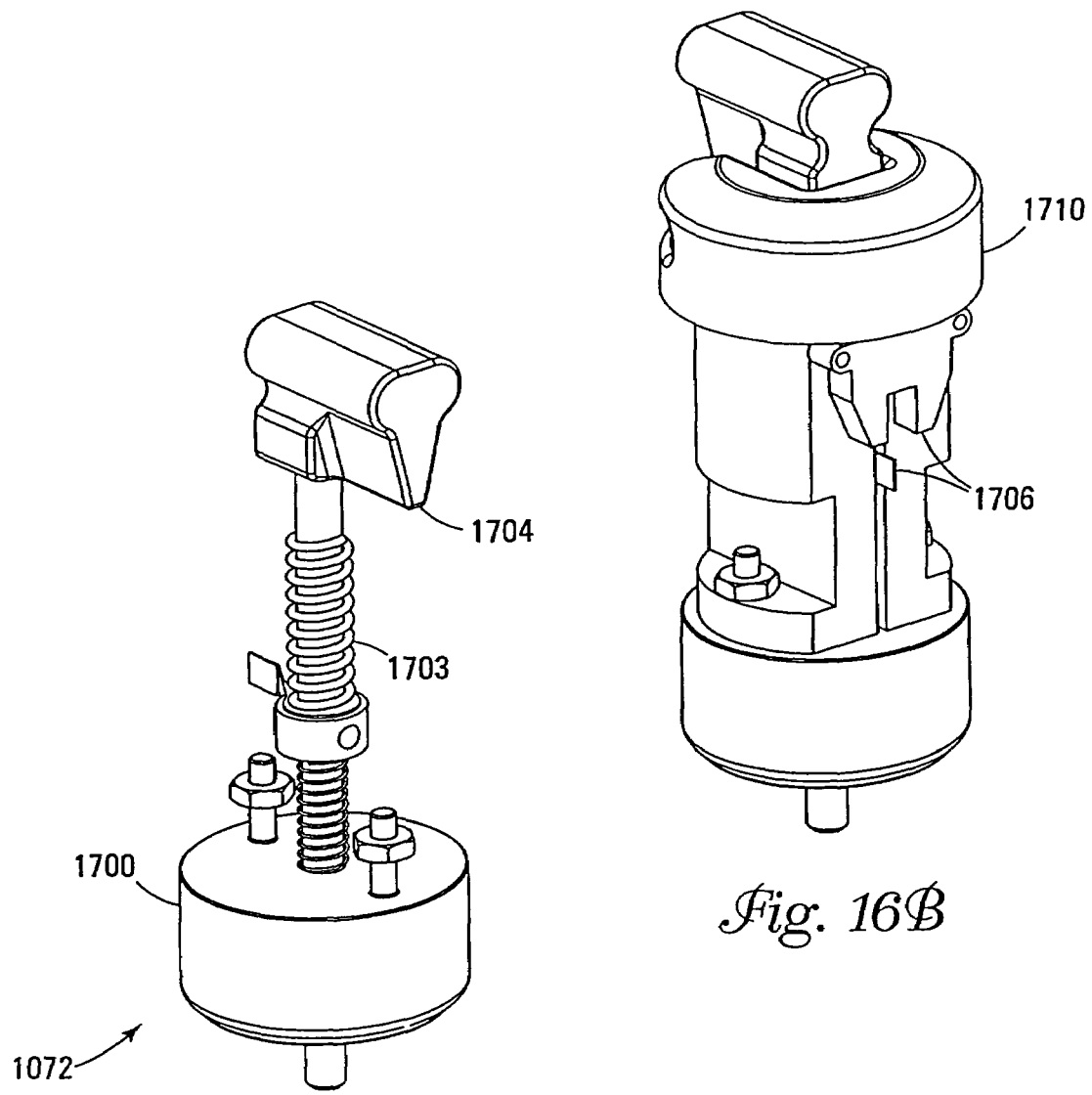
FIGS. 16A and 16B are perspective views of a pinch valve.
Figure 17:
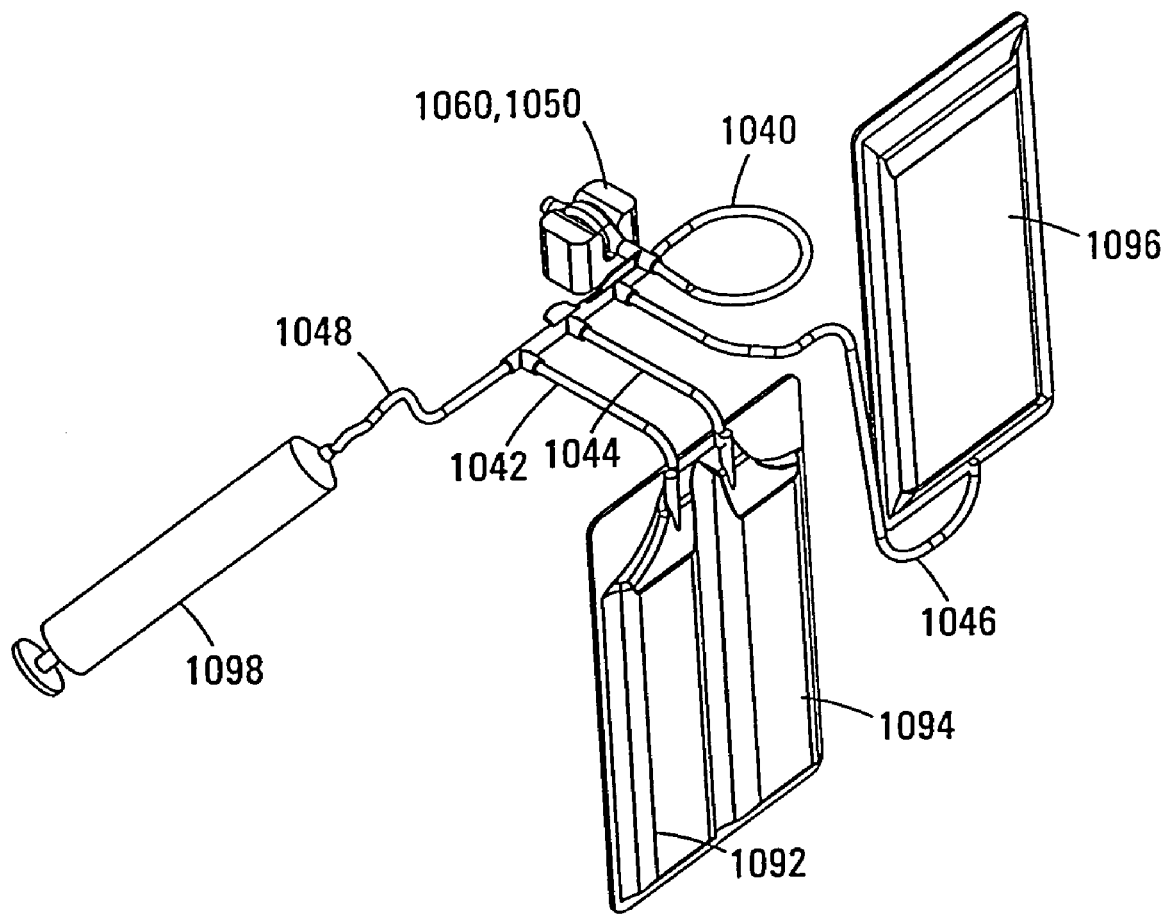
FIG. 17 is a perspective view of the disposable component of the apparatus of FIG. 15.

An alternate embodiment of this invention is illustrated in FIGS. 15 to 17. This apparatus functions similarly to the apparatus described above in FIGS. 1 to 14. FIG. 15 shows housing 1000 with display 1030. A separate reservoir 1096 for whole blood is provided and connected via tubing line 1046 to a common tubing line 1048 that is operably connected via pump loop 1040 to a pump (not shown) and to the centrifuge (not shown). Whole blood is sent to a variable volume separation chamber in the centrifuge where it is separated (as described above for the previous embodiment) and then the PPP and RBC components are sent to the reservoirs 1092 and 1094, respectively. PRP is collected by means of syringe 1098.

Fluid sensor pathway 1060 and sensors 1050 are directly in the line to/from the centrifuge. Three pinch valves 1072, 1074, and 1076 are provided in lines 1042, 1044, and 1046 that lead from the PPP, RBC, and WB reservoirs, respectively. These valves are operably connected to the sensors thereby automatically sending the desired fluid to the correct reservoir. For example, pinch valve 1072 is shown in FIGS. 16A and 16B. Pinch valve 1702 comprises solenoid 1700, pinch spring 1703, occluding edge of valve 1704, position sensor 1706, and housing 1710. FIG. 17 illustrates a disposable portion of apparatus 1000.

The above description and the drawings are provided for the purpose of describing embodiments of the invention and are not intended to limit the scope of the invention in any way. It will be apparent to those skilled in the art that various modifications and variations can be made without departing from the spirit or scope of the invention. Thus, it is intended that the present invention cover the modifications and variations of this invention provided they come within the scope of the appended claims and their equivalents.

What is claimed is:

1. A centrifuge apparatus for processing blood comprising
a bottom spring-loaded support plate;
a top support plate;
an axial inlet/outlet for blood to be processed and processed components of the blood, the axial inlet/outlet being attached to the top support plate by a rotating seal assembly;

a variable volume separation chamber mounted between the bottom support plate and the top support plate, the variable volume separation chamber being fluidly connected to the axial inlet/outlet;

a pump fluidly connected to the axial inlet/outlet; and a rotary drive unit attached to the bottom support plate, wherein the top support plate is fixed vertically and the bottom spring-loaded support plate is mounted on springs that maintain pressure on the variable volume separation chamber and allow the bottom support plate to move vertically, wherein the axial inlet/outlet is connected to a container for blood and to a plurality of containers for receiving separated components of the blood, and wherein the apparatus further comprises a multi-position valve for controlling intake of blood from the container for blood and outlet of processed blood components from the axial inlet/outlet to the plurality of containers for blood, wherein the multi-position valve has a first position in which only two separate fluid conduits are provided within the valve and a second position in which only one fluid conduit is provided within the valve, and wherein the variable volume separation chamber is a disk-shaped bag.

2. An apparatus of claim 1, wherein the top support plate is disposable.

3. An apparatus of claim 1, wherein the disk-shaped bag is disposable.

4. An apparatus of claim 1, wherein the pump is a peristaltic pump.

5. An apparatus of claim 1, wherein the rotary drive unit and the pump are both controlled automatically by a processing unit.

6. An apparatus of claim 1, wherein the multi-position valve has four positions.

7. An apparatus of claim 1, wherein the multi-position valve is controlled automatically by a processing unit.

8. An apparatus of claim 1, wherein the container for blood and the plurality of containers for receiving separated components of the blood are disposable.

9. An apparatus of claim 1, further comprising a sensor for detecting the presence of blood and blood components.

10. An apparatus of claim 1, wherein the rotating seal assembly comprises one or more one piece lip seals.

11. An apparatus of claim 1, wherein the bottom support plate comprises a graduated scale that shows the amount of fluid present in the variable volume separation chamber.

12. A method of processing blood comprising:

providing a centrifuge apparatus, the centrifuge apparatus comprising a bottom spring-loaded support plate;

a top support plate;

an axial inlet/outlet for blood to be processed and processed components of the blood, the axial inlet/outlet being attached to the top support plate by a rotating seal assembly;

a variable volume separation chamber mounted between the bottom support plate and the top support plate, the variable volume separation chamber being fluidly connected to the axial inlet/outlet;

a pump fluidly connected to the axial inlet/outlet; and a rotary drive unit attached to the bottom support plate, wherein the top support plate is fixed vertically and the bottom spring-loaded support plate is mounted on springs that maintain pressure on the variable volume separation chamber and allow the bottom support plate to move vertically, wherein the axial inlet/outlet is connected to a container for blood and to a plurality of containers for receiving separated components of the blood, and wherein the apparatus further comprises a multi-position valve for controlling intake of blood from the container for blood and outlet of processed blood components from the axial inlet/outlet to the plurality of containers for blood, wherein the multi-position valve has a first position in which only two separate fluid conduits are provided within the valve and a second position in which only one fluid conduit is provided within the valve, and wherein the variable volume separation chamber is a disk-shaped bag;

introducing a quantity of blood into the variable volume separation chamber;

centrifuging the blood; and removing the separated components of the blood through the axial inlet/outlet.

13. A method of claim 12, wherein the blood is centrifuged for from 5 to 15 minutes.

14. A method of claim 12, wherein the separated components of the blood are removed while the bottom support plate is still spinning.

15. A method of claim 12, wherein the quantity of blood introduced is from 20 to 200 ml.

16. A method of claim 12, wherein the top support plate is disposable.

17. A method of claim 12, wherein the disk-shaped bag is disposable.

18. A method of claim 12, wherein the pump is a peristaltic pump.

19. A method of claim 12, wherein the rotary drive unit and the pump are both controlled automatically by a processing unit.

20. A method of claim 12, wherein the multi-position valve has four positions.

21. A method of claim 12, wherein the multi-position valve is controlled automatically by a processing unit.

22. A method of claim 12, wherein the container for blood and the plurality of containers for receiving separated components of the blood are disposable.

23. A method of claim 12, further comprising a sensor for detecting the presence of blood and blood components.

24. A method of claim 12, wherein the rotating seal assembly comprises one or more one piece lip seals.

25. A method of claim 12, wherein the bottom support plate comprises a graduated scale that shows the amount of fluid present in the variable volume separation chamber.

26. A centrifuge apparatus for processing blood comprising a bottom support plate;

a top support plate;

an axial inlet/outlet for blood to be processed and processed components of the blood, the axial inlet/outlet being attached to the top support plate by a rotating seal assembly;

a variable volume separation chamber mounted between the bottom support plate and the top support plate, the variable volume separation chamber being fluidly connected to the axial inlet/outlet;

a pump fluidly connected to the axial inlet/outlet; and a rotary drive unit attached to the bottom support plate, wherein the top support plate is fixed vertically and the bottom support plate is mounted on a mechanical actuator that maintains pressure on the variable volume separation chamber and allows the bottom support plate to move vertically, wherein the axial inlet/outlet is connected to a container for blood and to a plurality of containers for receiving separated components of the blood, and wherein the apparatus further comprises a multi-position valve for controlling intake of blood from the container for blood and outlet of processed blood components from the axial inlet/outlet to the plurality of containers for blood, wherein the multi-position valve has a first position in which only two separate fluid conduits are provided within the valve and a second position in which only one fluid conduit is provided within the valve, and wherein the variable volume separation chamber is a disk-shaped bag.

27. An apparatus of claim 26, wherein mechanical actuator is controlled automatically by a processing unit.

* * * * *